US007219020B1

(12) United States Patent  
Hull et al.

(10) Patent No.: US 7,219,020 B1  
(45) Date of Patent: *May 15, 2007

(54) CHEMICAL STRUCTURE SIMILARITY RANKING SYSTEM AND COMPUTER-IMPLEMENTED METHOD FOR SAME

(75) Inventors: Richard D. Hull, Colts Neck, NJ (US); Eugene M. Fluder, Jr., Hamilton Square, NJ (US); Suresh B. Singh, Kendall Park, NJ (US); Robert P. Sheridan, Bloomfield, NJ (US); Robert B. Nachbar, Washington Crossing, NJ (US); Simon K. Kearsley, Westfield, NJ (US)

(73) Assignee: Axontologic, Inc., Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/546,399

(22) Filed: Apr. 10, 2000

Related U.S. Application Data

(60) Provisional application No. 60/128,473, filed on Apr. 9, 1999.

(51) Int. Cl.  
*G06F 17/16* (2006.01)
(52) U.S. Cl. ...................................................... 702/27
(58) Field of Classification Search .................. 702/27, 702/30; 707/6, 101; 708/402  
See application file for complete search history.

(56) References Cited

U.S. PATENT DOCUMENTS

| | | | | |
|---|---|---|---|---|
| 5,418,944 | A |   | 5/1995 | DiPace et al. .............. 395/800 |
| 5,577,239 | A |   | 11/1996 | Moore et al. ............... 395/603 |
| 5,604,686 | A |   | 2/1997 | Stewart ....................... 364/578 |
| 5,778,362 | A | * | 7/1998 | Deerwester .................... 707/5 |
| 5,878,373 | A |   | 3/1999 | Cohen et al. |
| 5,901,069 | A |   | 5/1999 | Agrafiotis et al. ..... 364/528.03 |
| 6,038,197 | A | * | 3/2000 | Sitton et al. ................... 367/38 |
| 6,185,506 | B1 | * | 2/2001 | Cramer et al. ................ 702/19 |
| 6,332,138 | B1 | * | 12/2001 | Hull et al. ....................... 707/5 |
| 6,356,864 | B1 | * | 3/2002 | Foltz et al. ..................... 704/1 |
| 6,542,903 | B2 | * | 4/2003 | Hull et al. ............... 707/104.1 |

FOREIGN PATENT DOCUMENTS

| | | |
|---|---|---|
| EP | 0829810 | 3/1999 |
| EP | 0510634 | 7/1999 |
| WO | WO-00/82251 | 1/2006 |

OTHER PUBLICATIONS

Alsberg et al. Molecular reference (MOLREF): A new tool in quantitative structure-activity relationships. Chamometrics and Intelligent Laboratory Systems. (1990) vol. 8, No. 2, pp. 173-181.*  
International Search Report PCT/US00/09385. Jul., 2000.  
Xie et al., An Efficient Projection Protocol for Chemical Databases: Singular Value Decomposition Combined with Truncated-Newton Minimization, J. Chem. Inf. Compt. Sci. 2000, 40, published on Web Dec. 1999, pp. 167-177.  
Kearsley et al., Chemical Similarity Using Physiochemical Property Descriptors, J. Chem. Inf. Comput. Sci. 1996, vol. 36, published Aug. 1996, pp. 118-127.  
Carhart et al., "Atom pairs as molecular features in structure-activity studies: definition and applications", J. Chem. Inf. Comp. Sci., 1985, 25:64-73.  
Nilakantan, R., et al., "Topological torsions: a new molecular descriptor for SAR applications. Comparison with other descriptors"., J. Chem. Inf. Comp. Sci. 1987, 27:82-85.  
Deerwester, S., et al., Indexing by Latent Semantic Analysis. J. American Society for Information Science, 1990, 41(6):391-407.  
Spear, K.L., et al., "Conformational restriction of angiotensin II: cyclic analogs having high potency.", J. Med. Chem., 1990, 33, 1935-1940.  
In re Schlittler and Uffer, 110 USPQ 304. Decided Jun. 21, 1956.

* cited by examiner

*Primary Examiner*—Marjorie A. Moran  
(74) *Attorney, Agent, or Firm*—Wilmer Cutler Pickering Hale and Dorr LLP

(57) ABSTRACT

A novel extension of the vector space model for computing chemical similarity is described. In one embodiment, a method calculates similarity between molecules and molecular descriptors using the singular value composition (SVD) of a molecule/descriptor matrix and, for example, an identity matrix, to create a low dimensional representation of the original descriptor space. Probe or query molecules then can be projected into the low dimensional representation and compared to the molecules from the original matrix.

2 Claims, 17 Drawing Sheets

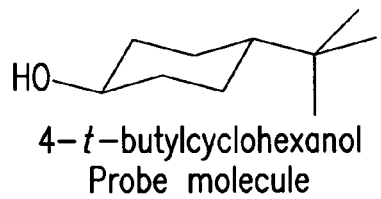
4-t-butylcyclohexanol
Probe molecule
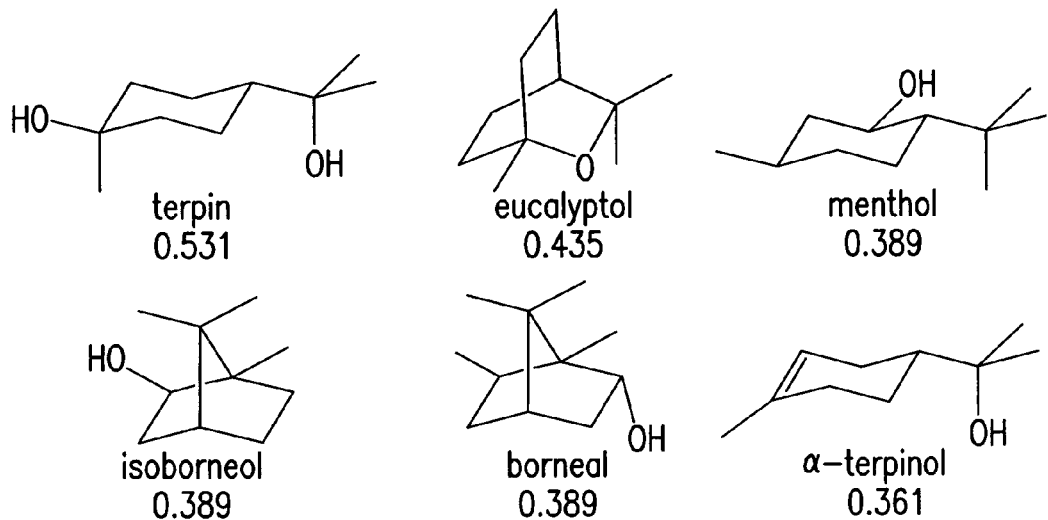
| terpin | eucalyptol | menthol |
| 0.531 | 0.435 | 0.389 |
| isoborneol | borneal | α-terpinol |
| 0.389 | 0.389 | 0.361 |
6 Most similar by Tanimoto similarity
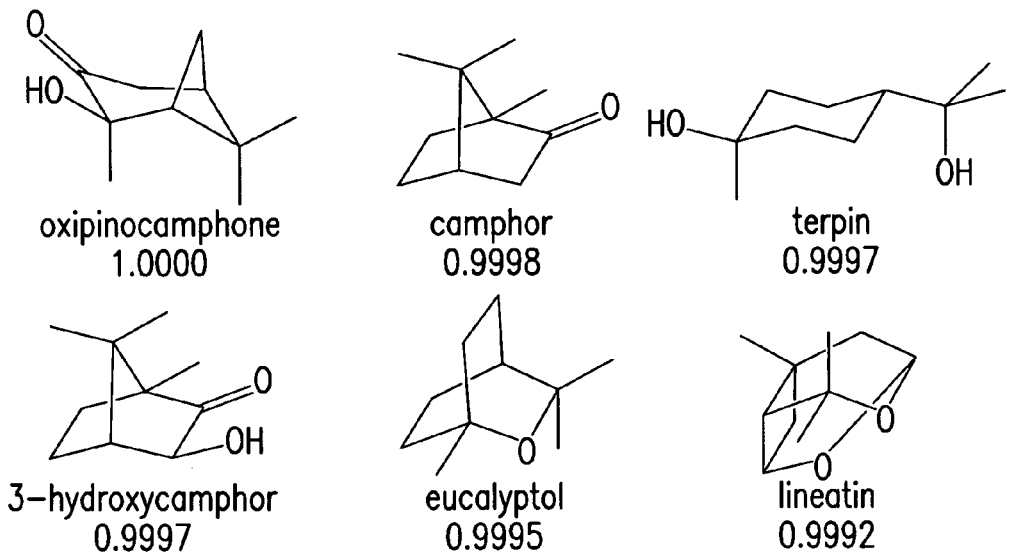
| oxipinocamphone | camphor | terpin |
| 1.0000 | 0.9998 | 0.9997 |
| 3-hydroxycamphor | eucalyptol | lineatin |
| 0.9997 | 0.9995 | 0.9992 |
6 Most similar by LaSSI similarity
FIG.2

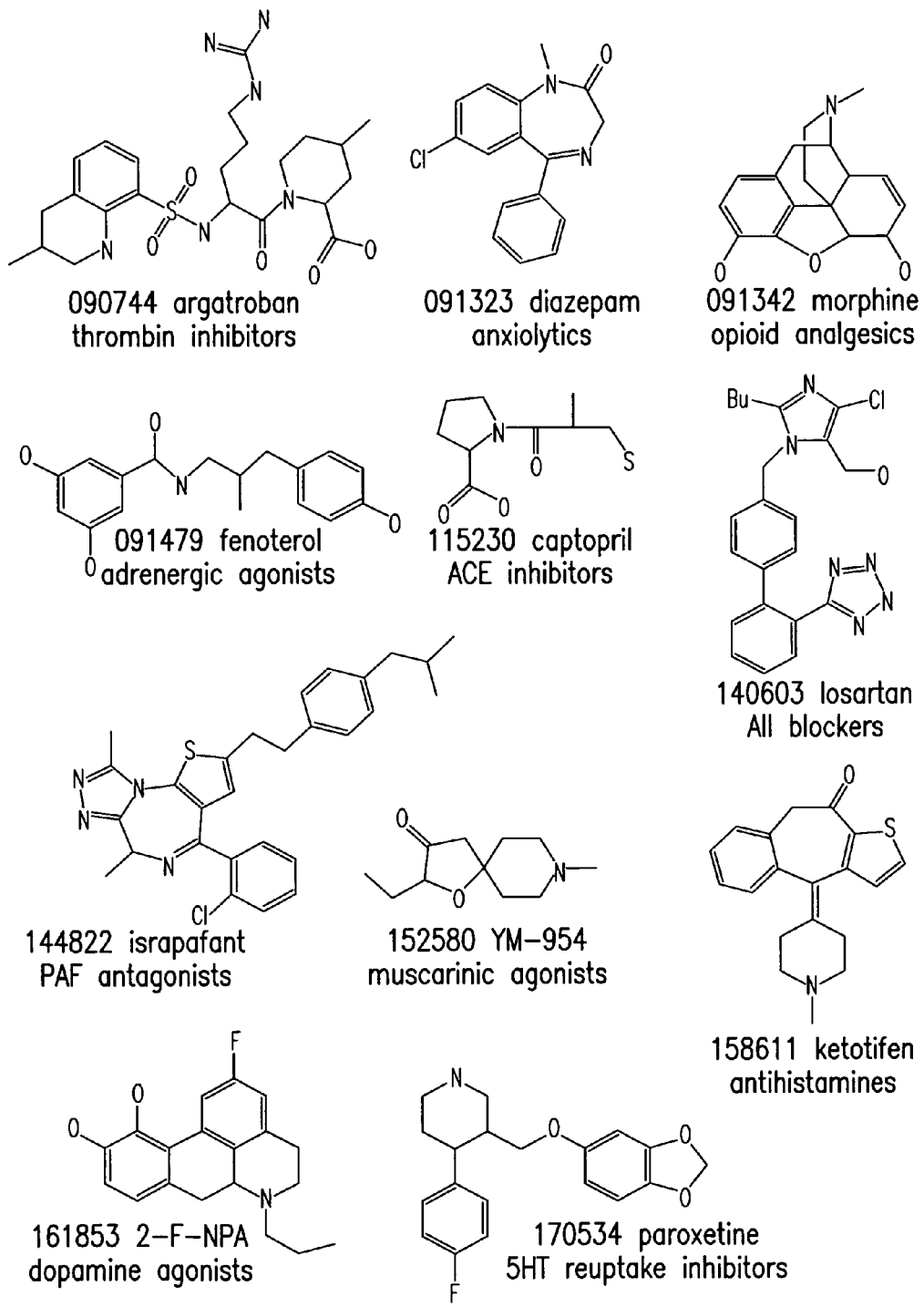

Standard probes used in this study. Each is labeled by the MDDR external registry, its name, and associated activity.

090744 argatroban
thrombin inhibitors 091323 diazepam
anxiolytics 091342 morphine
opioid analgesics 091479 fenoterol
adrenergic agonists 115230 captopril
ACE inhibitors 140603 losartan
AII blockers 144822 israpafant
PAF antagonists 152580 YM-954
muscarinic agonists 158611 ketotifen
antihistamines 161853 2-F-NPA
dopamine agonists 170534 paroxetine
5HT reuptake inhibitors

FIG.6a

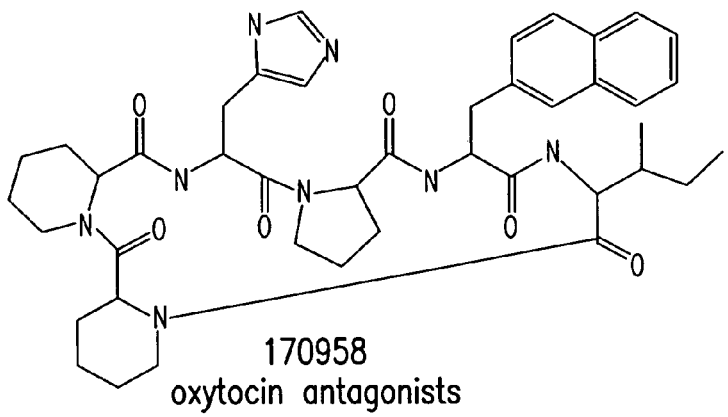
170958
oxytocin antagonists
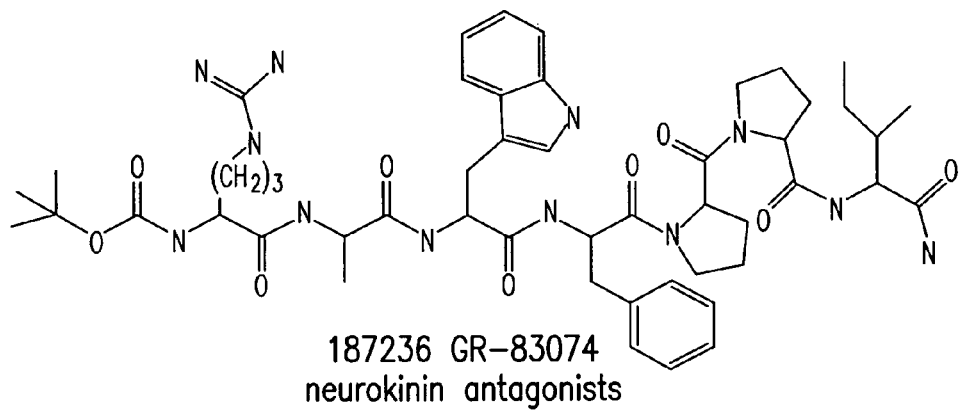
187236 GR-83074
neurokinin antagonists
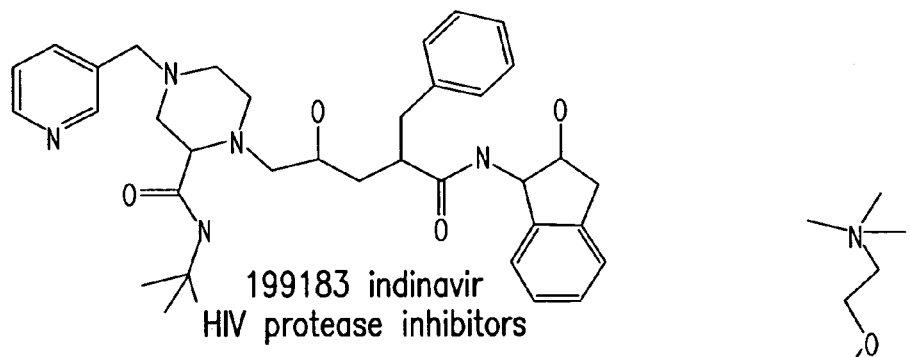
199183 indinavir
HIV protease inhibitors
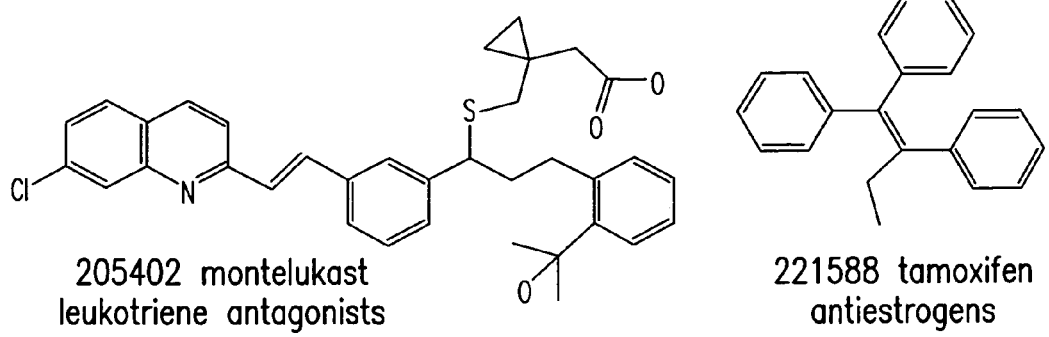
205402 montelukast
leukotriene antagonists
221588 tamoxifen
antiestrogens
FIG.6b Probes used for peptide -> non-peptide tests.
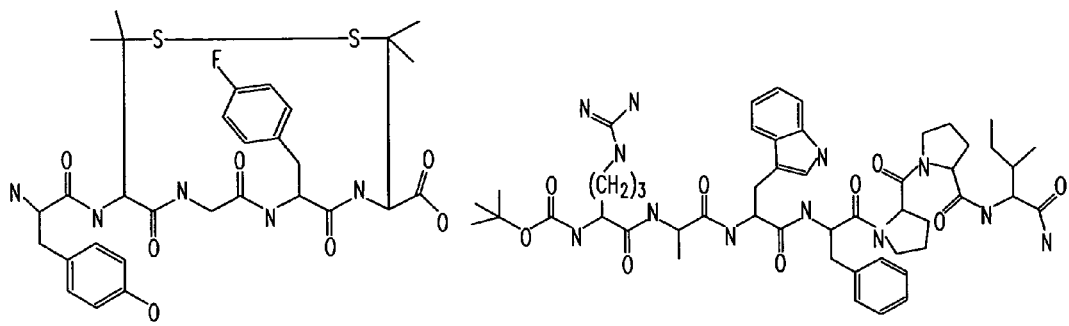
159880 F-DPDPE
opioid analgesics
187236 GR-83074
neurokinin antagonists
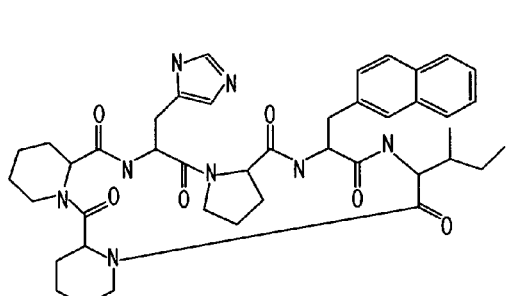
170958
oxytocin antagonists
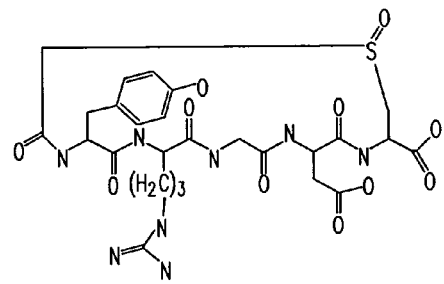
188541 G-4120
gpIIb/IIIa antagonists
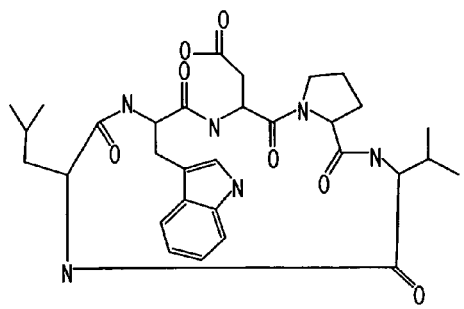
174556 BQ-123
endothelin antagonists
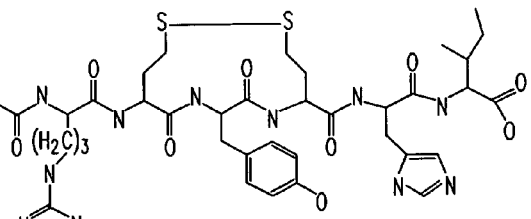
cycAII [Sar$^1$,Hcy$^{3,5}$,II$^8$]AII
AII blockers
FIG. 7

The correlation of rank for Dice APTT and LaSSI APTT. The example is 199183 using 170 singular values. Each circle represents a HIV protease inhibitor.

Selected compounds that have extremely different ranks in Dice APTT vs LaSSI APPT. The examples are 161853 with 800 singular values, 170534 with 150 singular values. The ranks in two types of search are indicated.

Mean similarity of the probe to each molecule in the top scoring 300 compounds (MSP300) for three samples. The MSP300 for Dice searches are shown as a horizontal lines. For comparison, the MSP300 for random sets of 300 compounds from MDDR would be 0.12–0.14.

Cumulative actives found vs compounds tested for 187236 as a probe.
The actives are oxytocin antagonists that do not contain a dipeptide moiety.

Selected non-peptide compounds that have extremely different ranks in Dice APTT vs LaSSI APTT for the statistically significant peptide to non-peptide examples.

174556 endothelin antagonists (9 SV's)

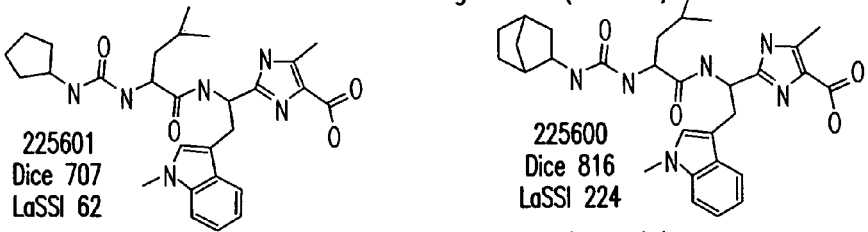

225601
Dice 707
LaSSI 62

225600
Dice 816
LaSSI 224

187236 neurokinin antagonists (2 SV's)

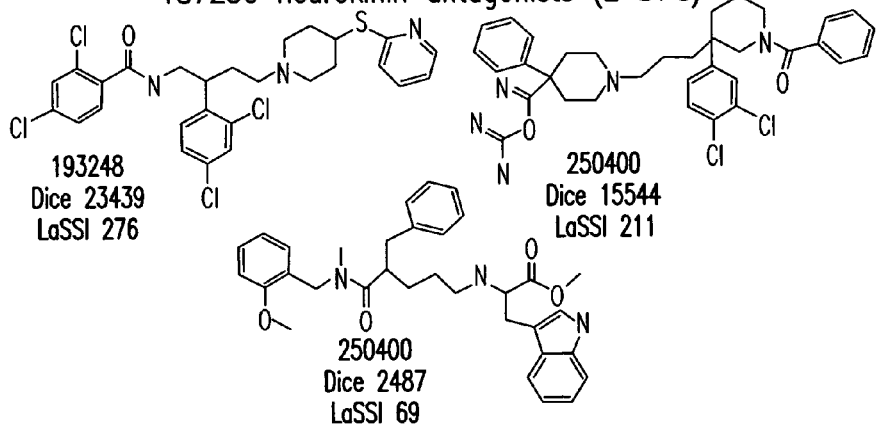

193248
Dice 23439
LaSSI 276

250400
Dice 15544
LaSSI 211

250400
Dice 2487
LaSSI 69

188541 gpIIb/IIIa receptor antagonists (15 SV's)

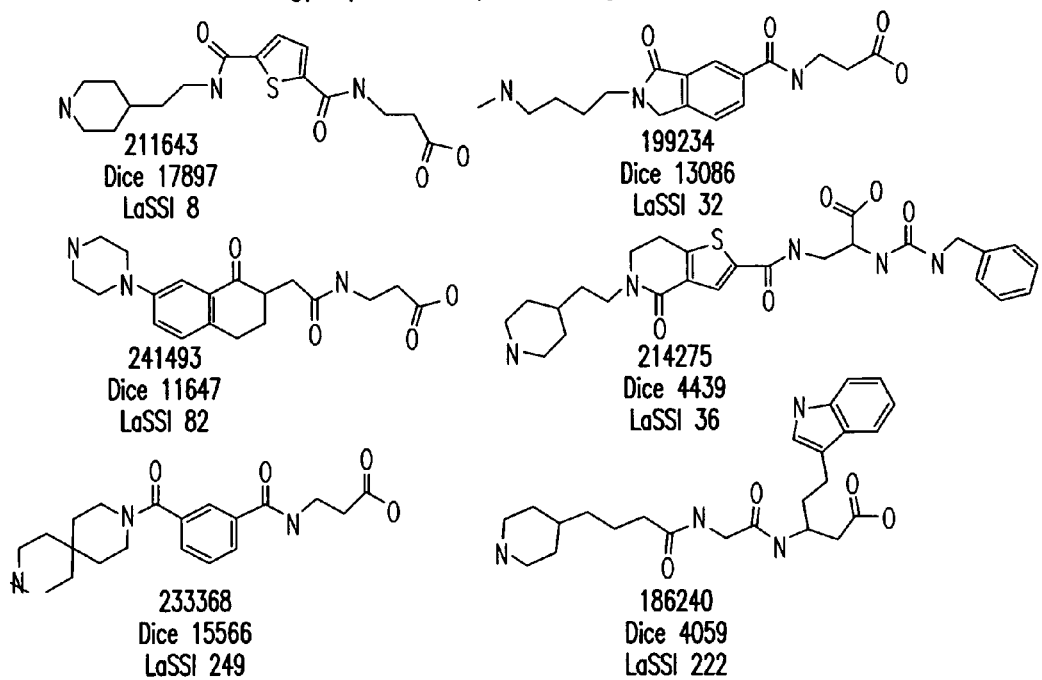

211643
Dice 17897
LaSSI 8

199234
Dice 13086
LaSSI 32

241493
Dice 11647
LaSSI 82

214275
Dice 4439
LaSSI 36

233368
Dice 15566
LaSSI 249

186240
Dice 4059
LaSSI 222

FIG.13

CHEMICAL STRUCTURE SIMILARITY RANKING SYSTEM AND COMPUTER-IMPLEMENTED METHOD FOR SAME

RELATED APPLICATIONS

This application claims benefit of U.S. Provisional Application Ser. No. 60/128,473, filed Apr. 9, 1999 and incorporated herein by reference.

FIELD OF THE INVENTION

This invention relates, in general, to computer-based calculation of compounds, compositions, mixtures, and/or chemical structure similarity and, in particular, to the ranking of compositions, mixtures, and/or chemical compounds, mixtures and/or compositions compounds in databases, such as chemical databases, by their similarity to a user's probe compound(s).

BACKGROUND OF THE INVENTION

Pharmaceutical companies, for example, have large collections of chemical structures, compounds, or molecules. One or more employees thereof will find that a particular structure in the collection has an interesting chemical and/or biological activity, for example, a property that could lead to a new drug, or a new understanding of a biological phenomenon.

Similarity searches are a standard tool for drug discovery. Given a compound with an interesting biological activity or property, compounds that are structurally similar to it are likely to have similar activities or properties. In practice, an investigator provides a probe and searches over a database of compounds to find those which are similar. He then selects some number of the similar compounds for further investigation.

Chemical similarity algorithms operate over representations of chemical structure based on various types of features called descriptors. Descriptors include the class of two dimensional representations and the class of three dimensional representations. Two dimensional representations include, for example, standard atom pair descriptors, standard topological torsion descriptors, standard charge pair descriptors, standard hydrophobic pair descriptors, and standard inherent descriptors of properties of the atoms themselves. By way of illustration, regarding the atom pair descriptors, for every pair of atoms in the chemical structure, a descriptor is established or built from the type of atom, some of its chemical properties, and its distance from the other atom in the pair.

Three dimensional representations include, for example, standard descriptors accounting for the geometry of the chemical structure of interest, as mentioned above. For instance, geometry descriptors take into account a first atom being a short distance away in three dimensions from a second atom, although the first atom may be twenty bonds away from the second atom. Topological similarity searches, especially those based on comparing lists of pre-computed descriptors, are computationally very inexpensive.

The vector space model of chemical similarity involves the representation of chemical compounds as feature vectors. Exemplary features include substructure descriptors, such as atom pairs and/or topological torsions. An example of an atom pair descriptor is described by Carhart et al. [1], and an example of a topological torsion descriptor is described by Nilakantan et al. [2]. Atom pair descriptors ("AP") are substructures of the form:

$$AT_i-(\text{distance})-AT_j$$

where "(distance)" is the distance in bonds between an atom of type $AT_i$ and an atom of type $AT_j$ along the shortest path. Topological torsion descriptors ("TT") are of the form:

$$AT_i-AT_j-AT_k-AT_l$$

where i, j, k, and l are consecutively bonded and distinct atoms. All of the AP's and/or TT's in a compound are counted to form a frequency vector. Similarity between two compounds is calculated as a function of their vectors. Although there are many standard similarity measures, e.g., Euclidean distance, Manhattan distance, Dice similarity coefficient, Tanimoto similarity coefficient, and cosine association coefficient [31], each involves the comparison of frequencies of matching descriptors in both vectors. However, we have determined that, as a consequence, if the probe has few descriptors in common with any one compound in the database, the search will be met with limited, or no, success.

Additionally, we have recognized that these searches are often more involved when the goal is to select compounds that have similar activity or properties, but not obviously similar structure. That is, we have identified a need to ascertain, from a large collection of chemical structures, compounds, or molecules, a set of diverse chemical structures, for example, that may look dissimilar from the original probe compound, but exhibit similar chemical or biological activity. We have recognized that although algorithms using, for example, Dice-type and/or Tanimoto-type coefficients, by design, yield compounds that are most similar to the probe compound, such algorithms may fail to provide compounds or chemical structures characterized by diversity relative to the probe compound.

With respect to a chemical example, if a particular compound were found to be a HIV inhibitor, we have recognized that it would be desirable to search a database of chemical compounds or compositions for HIV inhibitors that are related to the original HIV inhibitor. Specifically, these newly found HIV inhibitors may very well be dissimilar to the original HIV inhibitor probe. However, we have appreciated that being able to find one or more dissimilar HIV inhibitors quickly and effectively can mean billions of dollars in revenue resulting from exploitation of the dissimilar HIV inhibitors.

SUMMARY OF THE INVENTION

It is, therefore, a feature and advantage of the instant invention to provide a method and/or system for selecting chemical compounds that have similar biological or chemical activities or properties, but not necessarily obviously similar structures.

It is another feature and advantage of the instant invention to provide a method and/or system for ascertaining, from a large collection of chemical structures, compounds, or molecules, a set of diverse chemical structures, for example, that optionally look dissimilar from an original probe compound, but exhibits similar chemical or biological activity. A probe compound, for example, includes a chemical structure for which related or behaviorally similar chemical structures are sought.

It is an additional feature and advantage of the instant invention to provide a methodology for calculating the similarity of chemical compounds to chemical probes. The methodology includes the following sequential, non-sequential, or sequence independent steps. Chemical descriptors for each compound in a collection of compounds are generated or created. The descriptors for a given compound are represented as a vector of unique descriptor frequencies. The collection of compound vectors is represented as the column vectors of a molecule-descriptor matrix. The singular value decomposition of this matrix is performed to produce the singular matrices. The chemical descriptors for user probe compounds are generated or created. The descriptors of probe compounds are transformed into the same coordinate system as the compounds in the collection, called a pseudo-object using the singular matrices. The similarity of transformed probes to the compounds in the collection is calculated. A list of the compounds in the collection ranked by decreasing order of similarity to the probe(s) is returned or outputted.

Optionally, the step of creating descriptors for compounds in the collection and probe compounds involves the generation of atom pair and topological torsion descriptors from the chemical connection tables of the compounds. The step of creating descriptors for compounds in the collection includes the creation of an index of descriptors and an index of compounds in the collection.

Optionally, the molecule-descriptor matrix is denoted as X. The step of performing the singular value decomposition produces singular matrices as $X = P\Sigma Q^T$ of rank r, and a reduced dimension approximation of X defined as $X_k = P_k \Sigma_k Q^T_k$ k<<r, where P and Q are the left and right singular matrices representing correlations among descriptors and compounds respectively, and $\Sigma$ represents the singular values. The pseudo-object is denoted as $O_F$ and is calculated from a probe F by $O_F = F^T P_k \Sigma^{-1}_k$. The step of calculating the similarity between the pseudo-object $O_F$ and the compounds in collection is computed by taking the dot product of the normalized vector of $O_F$ with each normalized row of $P_k$.

The similarity calculating step includes calculating the cosine between the each pair of vectors. The reduced dimensional approximation of X is derived by setting the k+1 through r singular values of $\Sigma$ to zero. The similarities of the pseudo-object to compounds is calculated by setting the first k singular values of $\Sigma$ to one. The setting step includes using an identity matrix I.

It is another feature and advantage of the instant invention to provide a method of generating a searchable representation of chemical structures. The method includes the following sequential, non-sequential, or sequence independent steps. The method includes generating an index of unique features. The method also includes generating a feature-chemical structure matrix. The method further includes determining correlations between chemical structures based on the generated feature-chemical structure matrix for generating the searchable representation of the chemical structures.

The index of unique features include chemical descriptors. The method includes generating the chemical descriptors from connection tables prior to the index-generating step. The determining step includes performing singular value decomposition of the feature-chemical structure matrix. The chemical descriptors include at least one of atom pair descriptors, topological torsion descriptors, charge pair descriptors, hydrophobic pair descriptors, inherent atom property descriptors, and geometry descriptors.

It is another feature and advantage of the instant invention to provide a computer readable medium including instructions being executable by a computer, the instructions instructing the computer to generate a searchable representation of chemical structures. The instructions include generating an index of unique features. The instructions also include generating a feature-chemical structure matrix. The instructions further include determining correlations between chemical structures based on the generated feature-chemical structure matrix for generating the searchable representation of the chemical structures.

In the computer readable medium, the index of unique features include chemical descriptors. The method includes generating the chemical descriptors from connection tables prior to the index-generating step. The determining step includes performing singular value decomposition of the feature-chemical structure matrix. The chemical descriptors include at least one of atom pair descriptors, topological torsion descriptors, charge pair descriptors, hydrophobic pair descriptors, inherent atom property descriptors and geometry descriptors.

The instructions further include determining whether a user has input a query compound probe, generating chemical descriptors for the query compound probe, calculating similarities between the chemical descriptors for the query compound probe and the searchable representation of the chemical structures, and ranking the chemical structures by similarity to the query compound probe. The instructions optionally further include modifying the query compound probe based on the generated results for the original query compound probe.

The challenge of selecting functionally similar, yet structurally different compounds from a chemical database can be accomplished by using latent structures statistically derived from the chemical database. The idea is to exploit these structures or correlations among the original chemical descriptors present in the database to calculate the similarity between probe compound(s) and compounds in the database. This invention, called Latent Semantic Structure Indexing or LaSSI, embodies these ideas.

Ranking compounds to a probe compound using the similarity of the reduced dimensional descriptors versus the similarity of the original descriptors has several advantages including the following. Latent structure matching is more robust than descriptor matching, discussed hereinbelow. The choice of the number of singular values provides a rational way to vary the resolution of the search. Probes created from more than one molecule are optionally and advantageously handled. The reduction in the dimensionality of the chemical space increases searching speed.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

Notations and Nomenclature

The detailed descriptions which follow may be presented in terms of program procedures executed on a computer or network of computers. These procedural descriptions and representations are the means used by those skilled in the art to most effectively convey the substance of their work to others skilled in the art.

A procedure is here, and generally, conceived to be a self-consistent sequence of steps leading to a desired result. These steps are those requiring physical manipulations of physical quantities. Usually, though not necessarily, these quantities take the form of electrical or magnetic signals capable of being stored, transferred, combined, compared and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary, or desirable in most cases, in any of the operations described herein which form part of the present invention; the operations are machine operations. Useful machines for performing the operation of the present invention include general purpose digital computers or similar devices.

DESCRIPTION OF THE DRAWINGS

FIG. 2 shows a probe chemical structure and the six most similar compounds to that probe by each of the methods as described in the illustrative example;

FIG. 6a shows standard probes used in a comparison study;

FIG. 6b shows standard probes used in the comparison study;

FIG. 7 shows probes used for peptide to non-peptide tests;

FIG. 13 shows selected non-peptide compounds having different ranks according to the Dice and LaSSI methodologies;

DETAILED DESCRIPTION OF THE INVENTION

Figure 1:
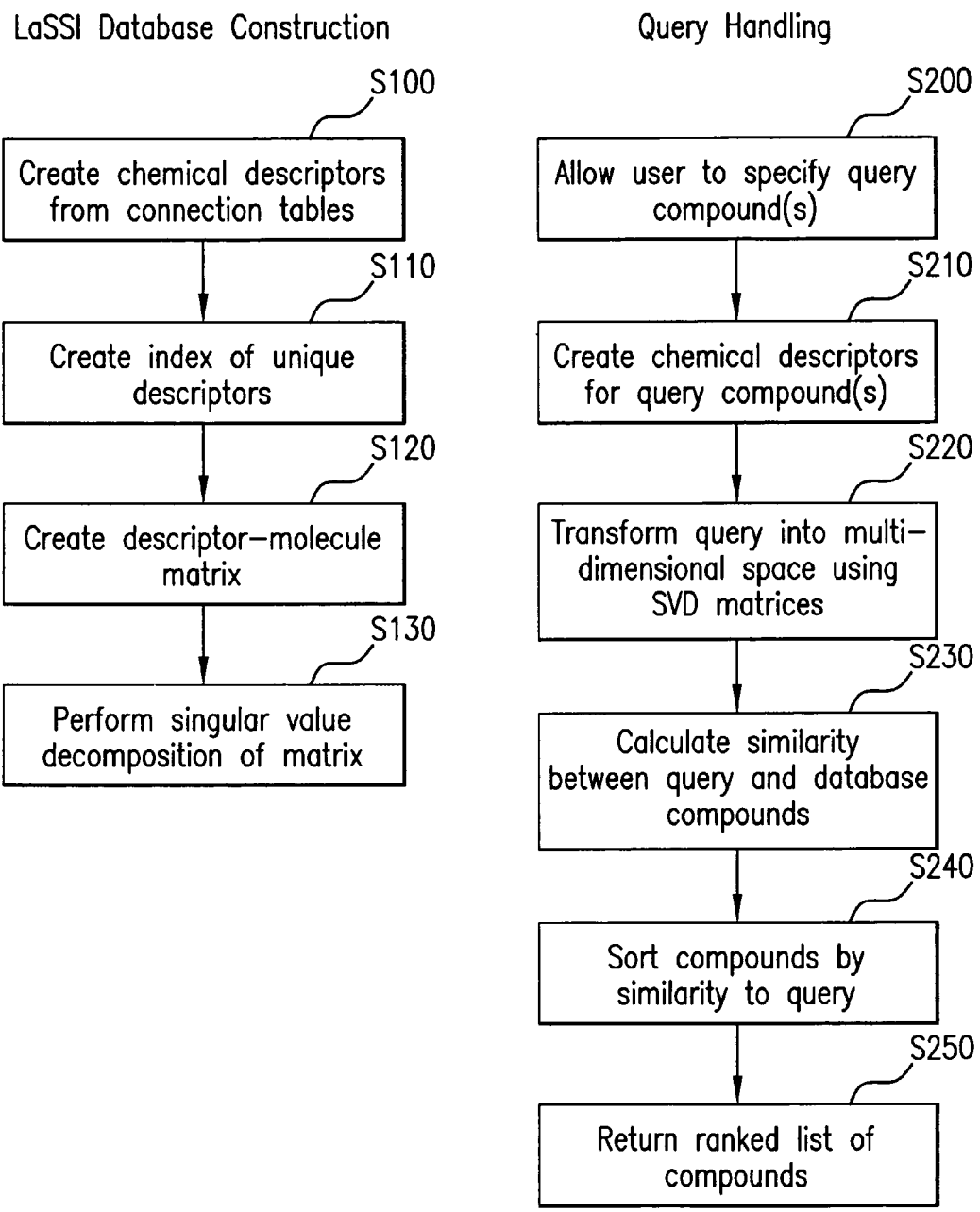
FIG. 1 is a flow chart depicting the processes of creating LaSSI databases and handling user probes.

A text metaphor is helpful to explain the shortcomings that we recognized in the existing search methods. A search for documents about cars from a collection of documents covering a range of topics may include a keyword query, such as, "car." However, a query limited to the word "car" will miss documents referring only to "automobile" because "car" and "automobile" are different descriptors and are not identical even though they define the same object. To uncover the relationship between "car" and "automobile," it may be noted that articles referring to cars also refer to gasoline, turnpikes, and steering wheels. It may also be noted that some or all of these terms are also found in articles referring to automobiles. Accordingly, a relationship or a pattern of association can be generated between articles referring to cars and those referring to automobiles. Thus, using such a technique, a search using a keyword query of "car" would yield articles referring to automobiles because it has been established that "car" and "automobile" are related.

In view of the above-mentioned shortcomings of existing search methods, we noted with interest U.S. Pat. No. 4,939,853 to Deerwester et al., incorporated herein by reference. This patent discloses a methodology for retrieving textual data objects. Deerwester et al. postulates that there is an underlying latent semantic structure in word usage data that is partially hidden or obscured by the variability of word choice. A statistical approach is utilized to estimate this latent semantic structure and uncover the latent meaning. That is, words, the text objects, and the user queries are processed to extract this underlying meaning and the new, latent semantic structure domain is then used to represent and retrieve information. However, Deerwester et al. fails to suggest any relevance to chemical structures, as neither a recognition of the instant need, nor a recognition of a solution thereto is addressed.

At a high level, the instant invention, which overcomes the above-mentioned shortcomings, is described as follows. We have determined that a standard mathematical technique called singular value decomposition ("SVD") facilitates the manipulation of key words or descriptors. A matrix representing every chemical structure, compound, or molecule in a database is generated using standard descriptors, as described by way of illustration above. At least some of the descriptors are correlated. The SVD technique uncovers these correlations or associations, which are used to rank the chemical structures, compounds, or molecules. Advantageously, the SVD method provides partial, if not full, credit for descriptors that are related, if not equivalent. That is, the descriptors need not be direct synonyms. Rather, they are optionally similar or related terms.

We have discovered that the SVD technique, as applied to a chemical context according to the instant invention, ranks highly chemical compounds or structures that do not directly appear to be similar at a superficial level, but are similar given the associations made in the database of chemical structures or compounds. By way of illustration, many organic compounds are built about carbon rings. In a six-membered ring, for example, using atom pair descriptors, not only is there always a carbon atom that is one bond away from another carbon atom, but also there is a carbon atom that is two bonds away from another carbon atom as well as a carbon atom that is three bonds away from another carbon atom. In view of this observation, we have recognized that these atom pairs are highly associated, although they are not conceptual synonyms. We have appreciated that the SVD technique facilitates ranking of chemical compounds or structures based on the number and/or degree of these associations.

The description of the inventive method can be further understood in the context of an illustrative example.

ILLUSTRATIVE EXAMPLE

To demonstrate the LaSSI method and to expose how it differs from standard vector model search techniques, we have created a small database of fifty-eight monoterpenes that can be examined in detail, as shown in FIG. 2, by way of illustration. Monoterpenes are small molecules, for example, ten carbon atoms arranged as two isoprene units, produced by plants, ostensibly to attract insects with their distinctive smells. Each compound is represented by a data structure called a connection table. Two-dimensional chemical descriptors, such as atom pair descriptors, are generated for each compound from their respective connection tables. Descriptors occurring in more than one compound are used to create an index of unique descriptors and a matrix relating descriptors to compounds, where the value of element (i,j) of the matrix is the frequency of descriptor i in compound j. Table 1 depicts a portion of the matrix created for the fifty-eight compounds.

TABLE 1

A Portion of the Descriptor-Molecule Matri for the 58 Monoterpene Example

|  | ascariodle | pulegone | thujic acid | ... | β-citral | o-cymene | p-cymene |
| --- | --- | --- | --- | --- | --- | --- | --- |
| APC10C1000 | 3 | 3 | 2 | ... | 3 | 3 | 3 |
| APC10C1002 | 1 | 1 | 1 | ... | 1 | 1 | 1 |
| APC10C1003 | 0 | 0 | 0 | ... | 0 | 0 | 0 |
| APC10C1004 | 0 | 0 | 0 | ... | 0 | 2 | 0 |
| APC10C1005 | 0 | 0 | 0 | ... | 0 | 0 | 0 |
| APC10C1006 | 2 | 2 | 0 | ... | 2 | 0 | 2 |
| APC11C1002 | 0 | 0 | 0 | ... | 0 | 0 | 0 |
| APC11C1003 | 0 | 0 | 0 | ... | 0 | 0 | 0 |
| APC11C1004 | 0 | 0 | 0 | ... | 0 | 0 | 0 |
| APC11C1006 | 0 | 0 | 0 | ... | 0 | 0 | 0 |
| APC11C1007 | 0 | 0 | 0 | ... | 0 | 0 | 0 |
| APC11C1100 | 0 | 0 | 0 | ... | 0 | 0 | 0 |
| APC20C1002 | 1 | 2 | 0 | ... | 1 | 0 | 0 |
| APC20C1003 | 3 | 3 | 0 | ... | 3 | 0 | 0 |
| APC20C1004 | 2 | 4 | 0 | ... | 2 | 0 | 0 |
| APC20C1006 | 0 | 0 | 0 | ... | 0 | 0 | 0 |
| APC20C1007 | 0 | 0 | 0 | ... | 0 | 0 | 0 |
| APC20C1102 | 0 | 0 | 0 | ... | 0 | 0 | 0 |
| APC20C1103 | 0 | 0 | 0 | ... | 0 | 0 | 0 |
| APC20C1104 | 0 | 0 | 0 | ... | 0 | 0 | 0 |
| . | . | . | . | . | . | . | . |
| . | . | . | . | . | . | . | . |
| . | . | . | . | . | . | . | . |
| APO20C1002 | 1 | 0 | 0 | ... | 0 | 0 | 0 |
| APO20C1003 | 3 | 0 | 0 | ... | 0 | 0 | 0 |
| APO20C1004 | 2 | 0 | 0 | ... | 0 | 0 | 0 |
| APO20C2001 | 0 | 0 | 0 | ... | 0 | 0 | 0 |
| APO20C2002 | 2 | 0 | 0 | ... | 0 | 0 | 0 |
| APO20C2003 | 2 | 0 | 0 | ... | 0 | 0 | 0 |
| APC20C2004 | 0 | 0 | 0 | ... | 0 | 0 | 0 |
| APC20C2101 | 0 | 0 | 0 | ... | 0 | 0 | 0 |
| APO20C2102 | 2 | 0 | 0 | ... | 0 | 0 | 0 |
| APO20C2103 | 2 | 0 | 0 | ... | 0 | 0 | 0 |
| APO20C2105 | 0 | 0 | 0 | ... | 0 | 0 | 0 |
| APO20C3002 | 1 | 0 | 0 | ... | 0 | 0 | 0 |
| APO20C3003 | 1 | 0 | 0 | ... | 0 | 0 | 0 |
| APO20C3101 | 0 | 0 | 0 | ... | 0 | 0 | 0 |

TABLE 1-continued

A Portion of the Descriptor-Molecule Matri for the 58 Monoterpene Example

| | ascariodle | pulegone | thujic acid | ... | β-citral | o-cymene | p-cymene |
|---|---|---|---|---|---|---|---|
| APO20C3102 | 0 | 0 | 0 | ... | 0 | 0 | 0 |
| APO20C3103 | 0 | 0 | 0 | ... | 0 | 0 | 0 |
| APO20C3104 | 0 | 0 | 0 | ... | 0 | 0 | 0 |
| APO20C4001 | 2 | 0 | 0 | ... | 0 | 0 | 0 |
| APO2001102 | 0 | 0 | 0 | ... | 0 | 0 | 0 |
| APO2002000 | 2 | 0 | 0 | ... | 0 | 0 | 0 |

Figure 3A:
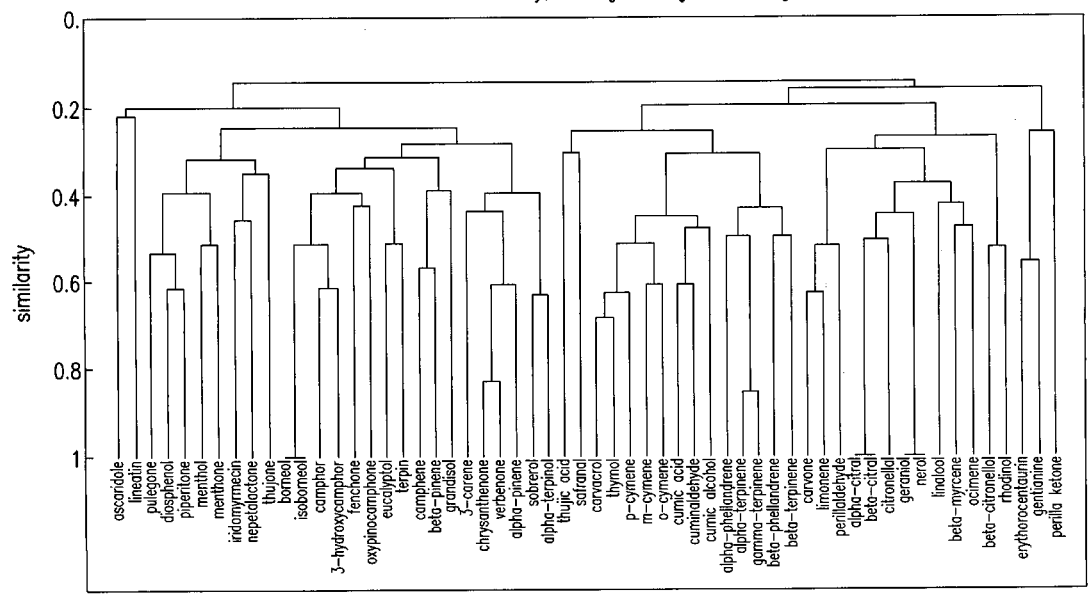
FIG. 3 shows a pair of dendrograms illustrating the self-similarity of the 58 compounds as determined by both of the methods described in the illustrative example.
Figure 3B:
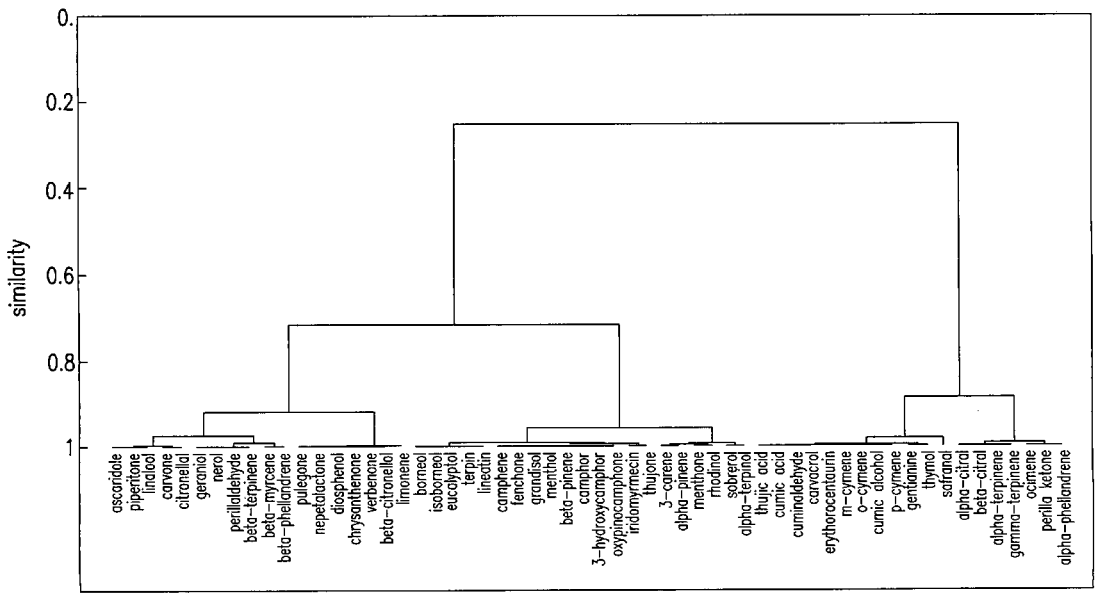

Performing a singular value decomposition of this matrix generates fifty-seven non-zero singular values and their corresponding singular vectors, or latent structures. The choice of the number of latent structures to use directly affects compound similarities. FIG. 3 depicts an example of a dendrogram using the vectors corresponding to the two largest singular values. The compounds form four highly-related groups. Similarities among compounds are shown graphically, by way of example, in FIG. 4 by treating the values of the two dimensions as spatial coordinates.

Figure 4:
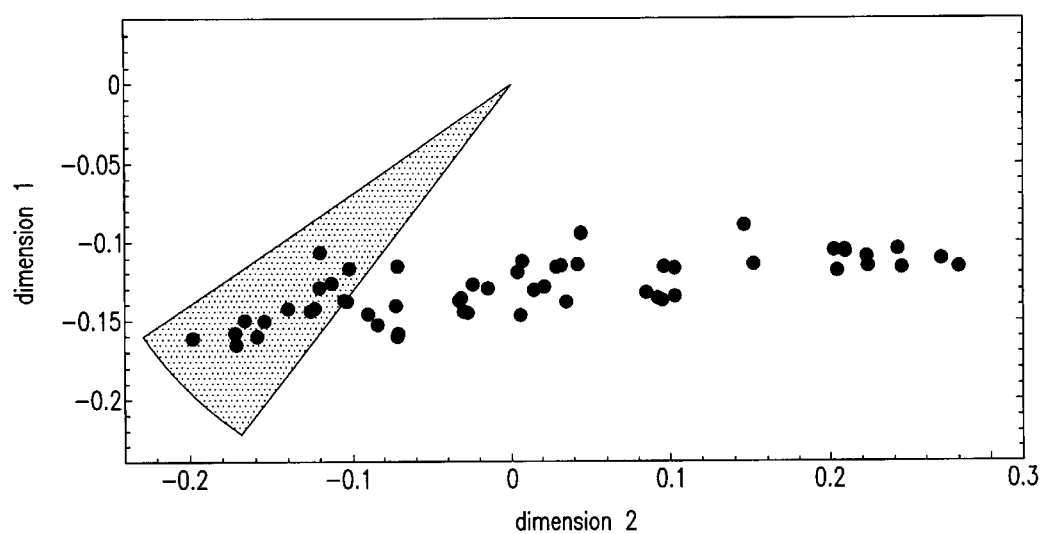
FIG. 4 is a plot of 58 compounds and the probe in the space of the first two singular vectors. The shaded region represents that area of space which is within 9° of the probe.

In FIG. 4, the fifty-eight monoterpenes are represented as filled circles. A probe compound, such as 4-t-butylcyclohexanol, which smells very much like camphor, but is not a monoterpene and is not part of the database, is represented as an open circle. Similarity between compounds is then calculated by computing the cosine of their position vectors in this two-dimensional space. The similarities of the fifty-eight compounds to the probe compound can also be easily calculated. The shaded region in FIG. 4 represents that area of space which is within 9° (2.5% of the unit circle) of the probe. Other suitable percentages are acceptable, depending on the desired amount of correlation between the database compound, and the probe compound. The six most similar monoterpenes shown in FIG. 2 which fall within this range are listed in Table 2.

TABLE 2

Six most similar compounds to probe selected by LaSSI

| LaSSI similarity | Compound |
|---|---|
| 0.999982 | oxypinocamphone |
| 0.999751 | camphor |
| 0.999702 | terpin |
| 0.999594 | 3-hydroxycamphor |
| 0.999450 | eucalyptol |
| 0.999079 | lineatin |

A traditional similarity measure, the Tanimoto similarity coefficient, would produce the similarities in Table 3.

TABLE 3

Six most similar compounds to probe selected by Tanimoto similarity

| Tanimoto similarity | Compound |
|---|---|
| 0.532 | terpin |
| 0.435 | eucalyptol |
| 0.389 | menthol |
| 0.389 | isoborneol |
| 0.389 | borneol |
| 0.361 | α-terpinol |

The advantage of this approach can be seen by comparing the ranks of camphor produced by the two approaches. Tanimoto similarity ranks $16^{th}$ (0.282), whereas LaSSI ranks it $2^{nd}$ (0.9997 or 1.2°). Although the Tanimoto similarity can rank compounds which share descriptors with the probe, it has no way of estimating the similarity of compounds which do not. LaSSI, on the other hand, does not suffer from this limitation.

Mathematical Background

The mathematical underpinnings of LaSSI were inspired by Latent Semantic Indexing (LSI), an information retrieval technique described in the Deerwester et al. article [4] and U.S. Pat. No. 4,839,853 to Deerwester et al., both incorporated herein by reference. LSI represents a collection of text documents as a term-document matrix for the purpose of retrieving documents from the collection given a user's query. LaSSI, on the other hand, uses a chemical descriptor-molecule matrix to calculate chemical similarities. Hence, the nature of the input matrices for LaSSI and LSI are very different. The mathematical treatment of these matrices, however, is the same. Later we will see that the calculation of object similarities made by LSI and LaSSI is related, but different.

LaSSI involves the singular value decomposition of a chemical descriptor-molecule matrix, X, where the column vectors of X describe each molecule. The SVD technique is well-known in the linear algebra literature and has been used in many engineering applications including signal and spectral analysis. Here we show a novel application of SVD to the problem of chemical similarity. For the purpose of this disclosure, the terms descriptors and molecules as the rows and columns of X, respectively, will be used interchangeably with the more general terms "features" and "objects".

Let the SVD of X in $R^{mxn}$ be defined as $X=P\Sigma Q^T$ where P is a standard mxr matrix, called the left singular matrix where r is the rank of X, and its columns are the eigenvectors of $XX^T$ corresponding to nonzero eigenvalues. Q is a nxr matrix, called the right singular matrix, whose columns are the eigenvectors of $X^TX$ corresponding to non-zero eigenvalues. $\Sigma$ is a rxr diagonal matrix=diag($\sigma_1, \sigma_2, \ldots, \sigma_r$) whose nonzero elements, called singular values, are the square roots of the eigenvalues and have the property that $\sigma 1 \geq \sigma 2 \geq \ldots \geq \sigma_r$. The $k^{th}$ rank approximation of X, $X_k$, for k<r, $\sigma_{k+1} \ldots \sigma_r$ set to 0, can be efficiently computed using variants of the standard Lasnczos algorithm (Berry, 1996). $X_k$ is the matrix of rank k which is closest to X in the least squares sense and is called a partial SVD of X and is defined as $X_k=P_k\Sigma_k Q^T_k$.

Given the partial SVD of X, similarities between features, between objects, and between a feature and an object are computed. Furthermore, we compute the similarity of ad hoc query objects, such as, column vectors which do not exist in X, to both the features and the objects in the database. The similarity of two features, $F_i$ and $F_j$, can be calculated by computing the dot product between the $i^{th}$ and $j^{th}$ rows of the matrix $P_k \Sigma_k$. The similarity of two objects, $O_i$ and $O_j$, can be calculated by computing the dot product between the $i^{th}$ and $j^{th}$ rows of the matrix $Q_k \Sigma^2_k$. The similarity of a feature, $F_i$, to an object, $O_j$, can be calculated by computing the dot product between the $i^{th}$ row of the matrix $P_k \Sigma^{1/2}_k$ and the $j^{th}$ row of the matrix $Q_k \Sigma^{1/2}_k$. Finally, the similarity of an ad hoc query to the features and objects in the databases can be calculated by first projecting it into the k-dimensional space of the partial SVD and then treating the projection as a "pseudo-object" for between and within comparisons. The pseudo-object of a query, F, is defined as $O_F = F^T P_k \Sigma^{-1}_k$.

Unlike LSI, however, LaSSI need not use the singular values to scale the singular vectors. Instead, the identity matrix I is used in place of $\Sigma_k$ for calculating similarities. This improves the system's ability to select functionally similar compounds from large chemical databases.

Methodology

There are two distinct phases of processing: 1) constructing a LaSSI version of a chemical database, and 2) calculating the similarity of probe molecule(s) to the compounds of the LaSSI database. The first phase is computationally expensive, however, it only needs to be performed once to create the database. The second phase, on the other hand, can be accomplished very quickly—a search of modest database (~$10^5$ compounds) can be performed in, for example, under two minutes using a standard computer. This section describes the details of both phases.

Constructing a LaSSI Database

Generating a LaSSI database includes the following sequential, non-sequential, or sequence independent steps. A user and/or a computer generates or creates chemical descriptors for each compound represented in the database in step S100. The user and/or the computer generates or creates an index relating the columns of the matrix to the compounds and another index relating the rows of the matrix to the chemical descriptors in step S110. The user and/or the computer generates or creates a chemical descriptor-molecule matrix representing the compounds in the chemical database in step S120. The user and/or the computer performs SVD on this matrix in step S130.

The creation of a descriptor-molecule matrix is provided by way of example as follows. First, one must decide on how molecules are to be represented, i.e., what descriptors are to be used. In our experience, two dimensional topological descriptors, such as atom pair (AP) and topological torsions (TT), have worked extremely well. We have also experimented with three dimensional geometric descriptors, combinations of two dimensional and three dimensional descriptors, and biological descriptors, all of which are acceptable according to the instant invention. However, for ease of understanding the instant invention, we will restrict our discussion of descriptors to only combinations of AP's and TT's. AP and TT descriptors are generated from the connection table of each compound in a chemical database. A first pass through the database is performed to create a catalog of unique descriptors and another catalog of each molecule. Then, a second pass creates a list of the frequency of each descriptor found in each molecule. Recall that the value of matrix element (i,j) of X is the frequency of descriptor i in molecule j.

The resulting matrix is used as input for public-domain SVD routines which produce the partial SVD of the matrix. We generally select the 1000 largest singular values and vectors for a LaSSI database. The database consists of the singular values and right and left singular vectors produced by the SVD.

Querying a LaSSI Database

Querying a LaSSI database is carried out as follows. A user specifies a single compound or multiple compounds as a probe in step S200. The connection table of a probe molecule, or multiple molecules in the case of a joint probe, is converted to the to descriptor set of the LaSSI database to create a feature, or column, vector for the probe in step S210. A pseudo-object is then obtained as described in the mathematics section above for some k, specified by the user in step S220. The normalized dot products of each molecule, i.e., each row of $P_k$, with the pseudo-object are calculated in step S230, and the resulting values are sorted in descending order in step S240, maintaining the index of the molecule responsible for that value. The user is then presented with a list of the top ranked molecules cutoff at a user defined threshold, e.g., the top 300 or 1000 compounds in step S250.

By varying the number of singular values, based at least in part on the choice of k, the user controls the level of fuzziness of the search. Larger values of k are less fuzzy than smaller values thereof.

Figure 5:
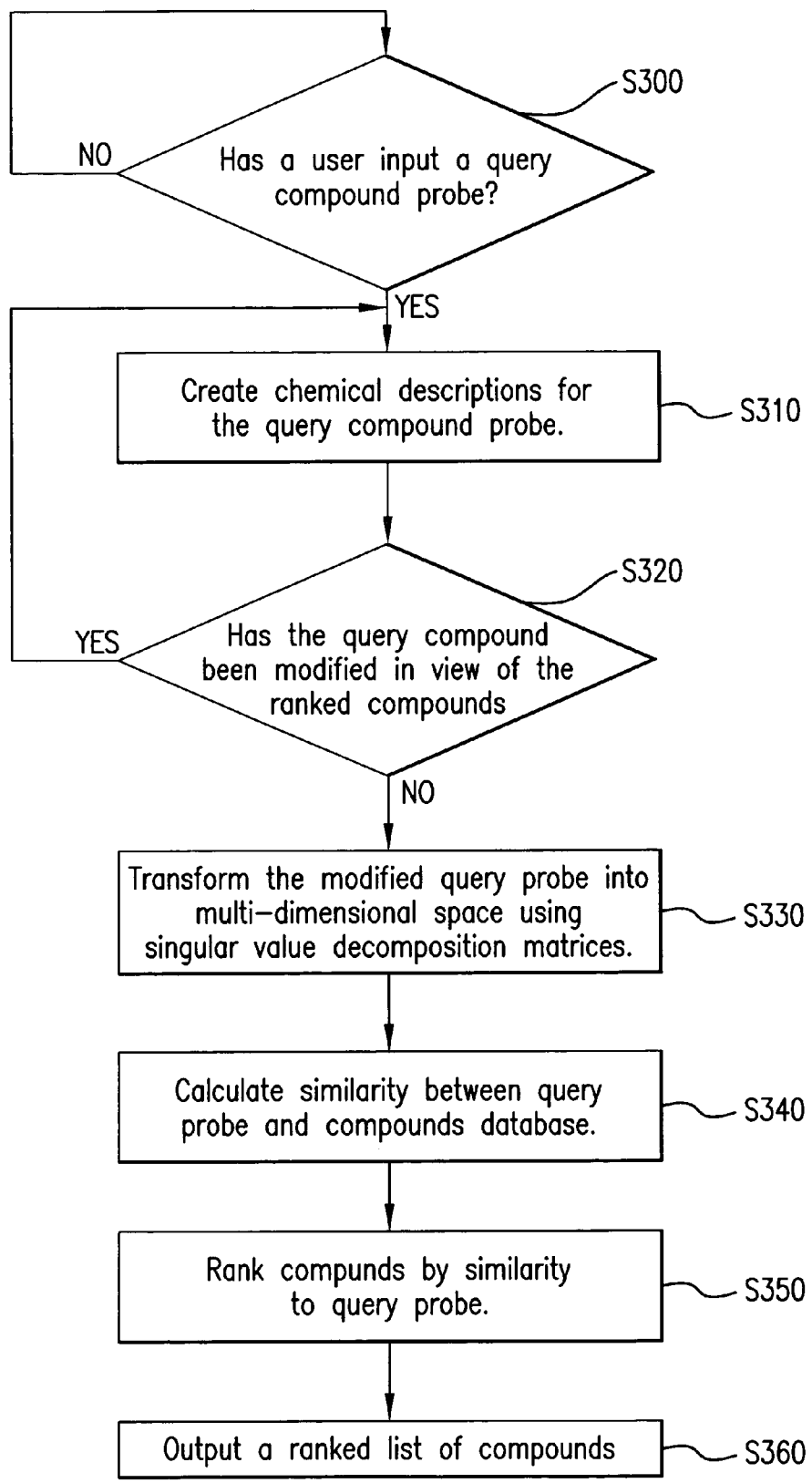
FIG. 5 is a flow chart of another embodiment of the instant invention.

FIG. 5 shows a flow chart of an alternative embodiment of a method consistent with the instant invention. The method includes the following sequential, non-sequential, or sequence independent steps. In step S300, a computer determines whether a user has input a query compound probe or query joint probe. If yes, in step S310, the computer generates chemical descriptors for the query compound probe or joint probe. In step S320, the computer determines whether the user has modified the query in view of the generated results. The user can select ranked compounds and add them to the original probe and re-execute the search. If yes, flow returns to step S310. Otherwise, in step S330, the computer transforms the modified query probe into multi-dimensional space using singular value decomposition matrices. In step S340, the computer calculates the similarity between the query probe and the chemical structures in the compounds database. In step S350, the computer ranks the compounds in the compound database by similarity to the query probe. In step S360, the computer outputs a ranked list of compounds in a standard manner, for example, via a standard computer monitor or via a standard printer.

LaSSI/TOPOSIM Comparison Study

The following includes results of a series of experiments comparing the LaSSI technology to one of Merck's existing screening systems, TOPOSIM. During this discussion, TOPOSIM will often be referred to by its default similarity metric, in this case "Dice" similarity.

Measures of Merit for Similarity Searches

In "Chemical Similarity Using Physiochemical Property Descriptors," J. Chem. Inf. Comput. Sci., 1996, 36, 118–127, Kearsley et al. [5], we proposed two measures of efficacy for similarity methods. The measures are based on a retrospective screening experiment. Imagine a database of N candidates. The candidates are ranked in order of decreasing similarity score. The candidate most similar to the probe is rank 1, the next rank 2, etc. The candidates are "tested" in order of increasing rank and the cumulative number of actives found is monitored as a function of candidates tested. The measures are as follows.
1) A first measure includes testing the number of compounds until half the actives are found. We called this number A50. A50 can be more usefully expressed as a global enhancement, the ratio of the A50 expected for the random case (N/2) over the actual A50.
2) A second measure includes finding/sending the number of actives after testing an arbitrary small fraction of the total database. For instance the number of actives at 300 compounds tested could be called A@300. A@300 is better expressed as an initial enhancement: the number of actives in the top ranked 300 compounds (ranked by the method under investigation) divided by the number of actives expected if the ranks of the actives were randomly assigned in the range 1 to N.

Diversity

Our objective is for LaSSI to find a more diverse set of actives than TOPOSIM, especially at ranks less than or equal to 300; Diverse in the sense that we want to see more actives that are not obvious analogs of the probe. We need a way to measure diversity to confirm this. There is an unavoidable circularity in comparing similarity methods by a diversity measure since diversity itself depends on a particular definition of similarity. Our resolution of this was to settle on the Dice similarity with the topological torsion ("TT") descriptor as a standard. In our earlier work, the TT was the least fuzzy descriptor and it has been our experience that only close analogs are recognized as very similar. One simple diversity measure, which we will call the MSP300, is defined as the mean Dice TT similarity of the probe with all the molecules in the top 300, not including the probe itself. One could do the same with only the actives in the top 300, but that would not be as useful because there are many situations where the number of such actives is very small.

Database Used in this Study

To measure the merit of the descriptors we need to have a database of molecules for which we know the biological activities. For this purpose, we use the MDL Drug Data Report ("MDDR") [6], which is a licensed database of drug-like molecules compiled from the patent literature. We constructed a database of ~82,000 standard molecules from MDDR, Version 98.2. Most structures have one or more key words in the "therapeutic category" field. We will assume that a molecule is active as an HIV protease inhibitor, for instance, if it contains the key word "HIV-1 protease inhibitor" in this field. There are some unavoidable limitations to using patent databases like MDDR. First, since not every compound has been tested in every area, one cannot assume that a compound without a particular key word is inactive. Thus, there may be some "false inactives." An opposite problem is that for some key words, not all actives work by the same mechanism as the probe (for instance by binding to the same receptor site) and we should not necessarily expect all actives to resemble the probe. Thus, there may also be some "false actives." However, comparisons between similarity methods should be valid, because for any given probe, the level of "noise" is the same for all methods.

Choice of Example Probes for Similarity Searches

In this comparison study, we will use two sets of probes. The first set is shown in FIGS. 6a and 6b. Table 4 shows how the activities were constructed from key words in MDDR.

TABLE 4

Probes and activity keywords used in this study.

| probe registration | nui probe name | Activity keywords from MDDR | Number of actives | |
|---|---|---|---|---|
| standard | | | | |
| 090744 | argtroban | thrombin inhibitor | 493 | |
| 091323 | diazepam | anxiolytic benzodiazepine benzodiazepine agonist | 3820 | |
| 091342 | morphine | analgesic, opioid opioid agonist kappa agonist delta agonist mu agonist | 869 | |
| 091479 | fenoterol | adrenergic (beta) agonist | 161 | |
| 115230 | captopril | ACE inhibitor | 490 | |
| 140603 | losartan | angiotensin II blocker | 2229 | |
| 144822 | israpafant | PAF antogonist | 1240 | |
| 152580 | YM-954 | muscarinic (M1) agonist | 858 | |
| 158611 | ketotifen | antihistaminic | 616 | |
| 161853 | 2-F-NPA | dopamine (D2) agonist | 127 | |
| 170534 | paroxetine | 5HT reuptake inhibitor | 219 | |
| 170958 | L-366948 | oxytocin antagonist | 176 | |
| 187236 | GR-83074 | neurokinin antagonist | 150 | |
| 199183 | indinavir | HIV-1 protease inhibitor | 641 | |
| 205402 | montelukast | leukotriene antagonist | 1165 | |
| 221588 | tamoxifen | antiestrogen | 233 | |
| peptide-> non-peptide | | | | |
| 159880 | F-DPDPE | opioid analgesics | 735 | non-peptide |
| 170958 | L-366948 | oxytocin antagonist | 159 | non-peptide |
| 174556 | BQ-123 | endothelin antagonist | 488 | non-peptide |
| 187236 | GR-83074 | neurokinin antagonist | 105 | non-peptide |

TABLE 4-continued

Probes and activity keywords used in this study.

| probe registration | nui probe name | Activity keywords from MDDR | Number of actives | |
|---|---|---|---|---|
| 188541 cycAII | G-4120 [Sar$^1$, Hcy$^{3,5}$, Ile$^8$]AII | gpIIb/IIIa receptor antagonist | 795 | non-peptide |

The probes and the corresponding therapeutic category in Table 4 were selected such that the following was true:
1) the probe itself was typical of a drug-like molecule or at least could be considered a plausible "lead;"
2) compounds in the same therapeutic category as the probe were fairly numerous and diverse; and
3) the therapeutic category was fairly specific, so that most of the molecules probably work by the same mechanism.

This was used for what could be considered "standard" similarity searching, wherein the idea is to search for actives which most resemble the probe. All actives from the MDDR are considered.

The second set of probes is in FIG. 7 and Table 4. Similar criteria were used to select them, except that these are exclusively peptide-like molecules (including two from the first set). A familiar example we wanted to include is angiotension II blockers, but MDDR does not contain a peptide antagonist. We therefore took the probe from Spear et al. [7]. These examples are used to test the ability of LaSSI to select non-peptide actives given a peptide probe. Therefore not all the actives in MDDR are considered, but only the non-peptide ones. There are many possible ways to define "non-peptide," but for our purposes we will consider a molecule a non-peptide if it does not include the substructure: N—Csp3-C(=O)—N—Csp3-C(=O).

Results of the Comparison Study

Measures of Merit for Standard Similarity Searches

Tables 5a and 5b list measures of merit for Dice relative to LaSSI with optimized singular values. The last row of the global enhancement table and the initial enhancement table shows the enhancement averaged over all of the probes. This number can be taken as a qualitative measure of goodness or efficacy of the method.

TABLE 5a

Measures of merit for Dice and LASSI where the number of singular values is optimized.

| Probe/ Activity | Dice AP | LaSSI AP | best no. SV's AP | Dice TT | LaSSI TT | best no. SV's TT | Dice APTT | LaSSI APTT | best no. SV's APTT |
|---|---|---|---|---|---|---|---|---|---|
| 090744 thrombin inhibitors | 55.7 | 35.8 | 160 | 33.7 | 19.0 | 290 | 71.6 | 53.2 | 170 |
| 091323 anxiolytics | 1.3 | 1.1 | 320 | 1.5 | 1.1 | 20 | 1.5 | 1.1 | 220 |
| 091342 opioid analgesics | 2.2 | 1.6 | 800 | 1.1 | 3.3 | 40 | 1.7 | 1.7 | 470 |
| 091479 adrenergic agonists | 1.5 | 28.7 | 330 | 27.3 | 77.3 | 220 | 9.4 | 14.6 | 170 |
| 115230 ACE inhibitors | 18.7 | 14.2 | 1000 | 18.1 | 17.2 | 650 | 18.7 | 17.8 | 950 |
| 140603 AII blockers | 36.7 | 36.0 | 100 | 36.6 | 35.7 | 110 | 36.9 | 36.1 | 100 |
| 144822 PAF antagonists | 2.5 | 1.7 | 970 | 1.4 | 1.3 | 260 | 2.0 | 1.9 | 850 |
| 152580 muscarinic agonists | 12.8 | 16.1 | 100 | 6.3 | 4.7 | 20 | 13.5 | 14.4 | 70 |
| 158611 antihistamines | 2.1 | 2.3 | 430 | 1.4 | 2.0 | 260 | 1.6 | 2.0 | 430 |
| 161853 dopamine agonists | 4.5 | 7.1 | 760 | 4.6 | 27.5 | 80 | 5.9 | 6.6 | 800 |
| 170534 5HT reuptake inhibitors | 3.2 | 2.0 | 300 | 1.6 | 0.9 | 170 | 2.5 | 2.5 | 150 |
| 170958 oxytocin antagonists | 2.8 | 2.2 | 100 | 1.8 | 3.0 | 260 | 2.5 | 1.7 | 510 |

TABLE 5a-continued

Measures of merit for Dice and LASSI where the number of singular values is optimized.

| Probe/ Activity | Dice AP | LaSSI AP | best no. SV's AP | Dice TT | LaSSI TT | best no. SV's TT | Dice APTT | LaSSI APTT | best no. SV's APTT |
|---|---|---|---|---|---|---|---|---|---|
| 187236 neurokinin antagonist | 4.3 | 1.8 | 90 | 3.7 | 2.3 | 5 | 4.6 | 7.1 | 100 |
| 199183 HIV protease inhibitors | 22.1 | 20.4 | 60 | 17.2 | 6.5 | 260 | 21.5 | 10.9 | 160 |
| 205402 leukotriene antagonists | 8.7 | 7.2 | 50 | 6.1 | 3.2 | 220 | 9.2 | 3.1 | 420 |
| 221588 antiestrogens | 2.9 | 4.1 | 300 | 2.9 | 3.1 | 270 | 3.7 | 5.2 | 650 |
| mean | 11.4 | 11.4 | | 10.3 | 13.0 | | 12.9 | 11.2 | |

TABLE 5b

Initial enhancement (@300) optimized singular values

| Probe/ Activity | Dice AP | LaSSI AP | best no. SV's AP | Dice TT | LaSSI TT | best no. SV's TT | Dice APTT | LaSSI APTT | best no. SV's APTT |
|---|---|---|---|---|---|---|---|---|---|
| 090744 thrombin inhibitors | 90.2 | 70.0 | 160 | 89.1 | 75.1 | 290 | 109.2 | 83.5 | 170 |
| 091323 anxiolytics | 4.7 | 6.2 | 320 | 4.4 | 4.3 | 20 | 5.7 | 6.9 | 220 |
| 091342 opioid analgesics | 17.5 | 23.2 | 800 | 30.8 | 26.1 | 40 | 30.2 | 30.2 | 470 |
| 091479 adrenergic agonists | 32.6 | 34.3 | 330 | 44.6 | 72.1 | 220 | 37.7 | 42.9 | 170 |
| 115230 ACE inhibitors | 34.9 | 76.1 | 1000 | 29.3 | 47.9 | 650 | 34.9 | 71.6 | 950 |
| 140603 AII blockers | 37.2 | 37.2 | 100 | 37.2 | 37.2 | 110 | 37.2 | 37.3 | 100 |
| 144822 PAF antagonists | 23.2 | 29.6 | 970 | 32.1 | 34.1 | 260 | 31.2 | 32.7 | 850 |
| 152580 muscarinic agonists | 46.0 | 49.9 | 100 | 29.9 | 36.7 | 20 | 45.1 | 51.2 | 70 |
| 158611 antihistamines | 30.0 | 44.8 | 430 | 51.6 | 59.2 | 260 | 44.8 | 50.7 | 430 |
| 161853 dopamine agonists | 17.4 | 84.8 | 760 | 50.0 | 60.9 | 80 | 34.8 | 78.3 | 800 |
| 170534 5HT reuptake inhibitors | 18.9 | 18.9 | 300 | 5.0 | 7.6 | 170 | 7.6 | 22.7 | 150 |
| 170958 oxytocin antagonists | 20.4 | 23.54 | 100 | 21.9 | 18.8 | 260 | 20.4 | 23.5 | 510 |
| 187236 neurokinin antagonist | 11.0 | 16.7 | 90 | 12.9 | 14.7 | 5 | 12.9 | 27.6 | 100 |
| 199183 HIV protease inhibitors | 55.6 | 56.0 | 60 | 60.3 | 69.8 | 260 | 62.9 | 58.2 | 160 |
| 205402 leukotriene antagonists | 37.2 | 37.9 | 50 | 42.9 | 33.0 | 220 | 44.1 | 35.8 | 420 |
| 221588 antiestrogens | 54.5 | 51.0 | 300 | 53.3 | 47.4 | 270 | 66.4 | 65.2 | 650 |
| mean | 33.2 | 41.8 | 366 ± 321 | 37.2 | 40.3 | 195 ± 154 | 39.1 | 44.9 | 388 ± 284 |

Figure 8:
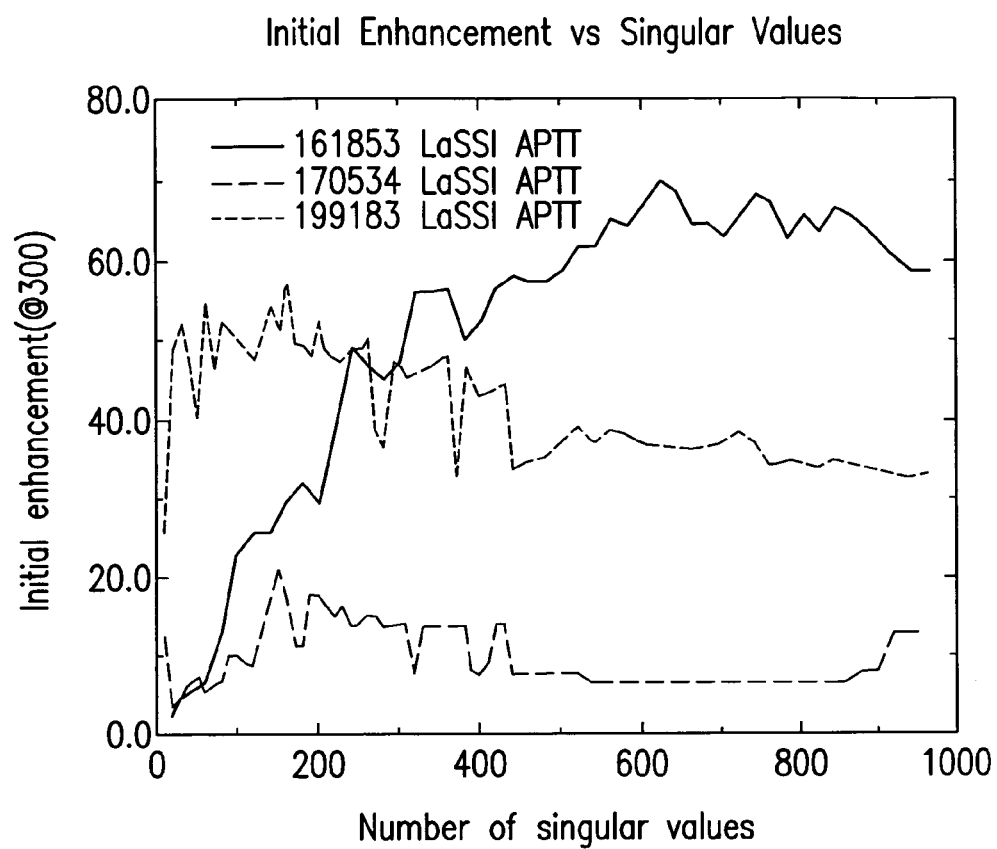
FIG. 8 is an initial enhancement graph.

In Table 5a, no clear superiority of TOPOSIM over LaSSI for the global enhancement example is evidenced, and no clear advantage to using atom pairs and topological torsions together ("APTT") relative to atom pairs ("AP") and topological torsions ("TT") individually. However, with reference to Table 5b, for initial enhancement, we have determined that there is a clear advantage of LaSSI over TOPOSIM. We believe that this advantage may result at least in part because the number of singular values was adjusted to maximize the initial enhancement. We have also measures of merit are to the number of singular values. FIG. 8 shows the initial enhancement as a function of number of singular values for three examples. The results can be somewhat sensitive to the number of singular values and different examples may show different sensitivities. If one is to pick a number of singular values to start with, one might pick 400, a number near 388, the mean optimum number of singular values over the examples. Table 6 compares the measures of merit for the optimized number of singular values vs 400 singular values.

TABLE 6

Enhancements for the best number of singular values vs 400 singular values.

| Probe/Activity | Dice APTT | global enhance LaSSI APTT best no. | LaSSI APTT 400 SV | Dice APTT | initial enhance LaSSI APTT best no. SV's | LaSSI APTT 400 SV | best no. SV's |
|---|---|---|---|---|---|---|---|
| 090744 thrombin inhibitors | 71.6 | 53.2 | 6.4 | 109.2 | 83.5 | 57.1 | 170 |
| 091323 anxiolytics | 1.5 | 1.1 | 1.1 | 5.7 | 6.9 | 5.6 | 220 |
| 091342 opioid analgesics | 1.7 | 1.7 | 1.3 | 30.2 | 30.2 | 28.0 | 470 |
| 091479 adrenergic agonists | 9.4 | 14.6 | 34.9 | 37.7 | 42.9 | 27.4 | 170 |
| 115230 ACE inhibitors | 18.7 | 17.8 | 15.1 | 34.9 | 71.6 | 45.1 | 950 |
| 140603 AII blockers | 36.9 | 36.1 | 30.0 | 37.2 | 37.3 | 37.2 | 100 |
| 144822 PAF antagonists | 2.0 | 1.9 | 1.6 | 31.2 | 32.7 | 29.4 | 850 |
| 152580 muscarinic agonists | 13.5 | 14.4 | 3.0 | 45.1 | 51.2 | 33.2 | 70 |
| 158611 antihistamines | 1.6 | 2.0 | 1.9 | 44.8 | 50.7 | 50.2 | 430 |
| 161853 dopamine agonists | 5.9 | 6.6 | 11.6 | 34.8 | 78.3 | 54.4 | 800 |
| 170534 5HT reuptake inhibitors | 2.5 | 2.5 | 1.7 | 7.6 | 22.7 | 8.8 | 150 |
| 170958 oxytocin antagonists | 2.5 | 1.7 | 2.1 | 20.4 | 23.5 | 22.0 | 510 |
| 187236 neurokinin antagonist | 4.6 | 7.1 | 7.8 | 12.9 | 27.6 | 20.3 | 100 |
| 199183 HIV protease inhibitors | 21.5 | 10.9 | 4.8 | 62.9 | 58.2 | 43.1 | 160 |
| 205402 leukotriene antagonists | 9.2 | 3.1 | 3.1 | 44.1 | 35.8 | 35.6 | 420 |
| 221588 antiestrogens | 3.7 | 5.2 | 3.0 | 66.4 | 65.2 | 51.0 | 650 |
| mean | 12.9 | 11.2 | 8.1 | 39.1 | 44.9 | 34.3 | | recognized a clear advantage in using combination descriptors for both Dice and LaSSI. The optimum number of singular values for LaSSI varies from as low as 5 to 1000 singular values for AP and TT descriptors and from 70 to 950 for APTT. Henceforth, when comparing Dice and LaSSI, we will consider only the APTT combination since it appears to yield the optimum or substantially optimum results.

In a real example, a user would not know the actives in advance. It is therefore important to know how sensitive the For about a third of the probes there is a significant degradation of the initial enhancement at 400 singular values. These are not necessarily the ones where the best number of singular values differs the most from 400, however. The degradation at 400 singular values is never so bad that LaSSI is rendered useless.

Correlation of Ranks Between Descriptors

Figure 9:
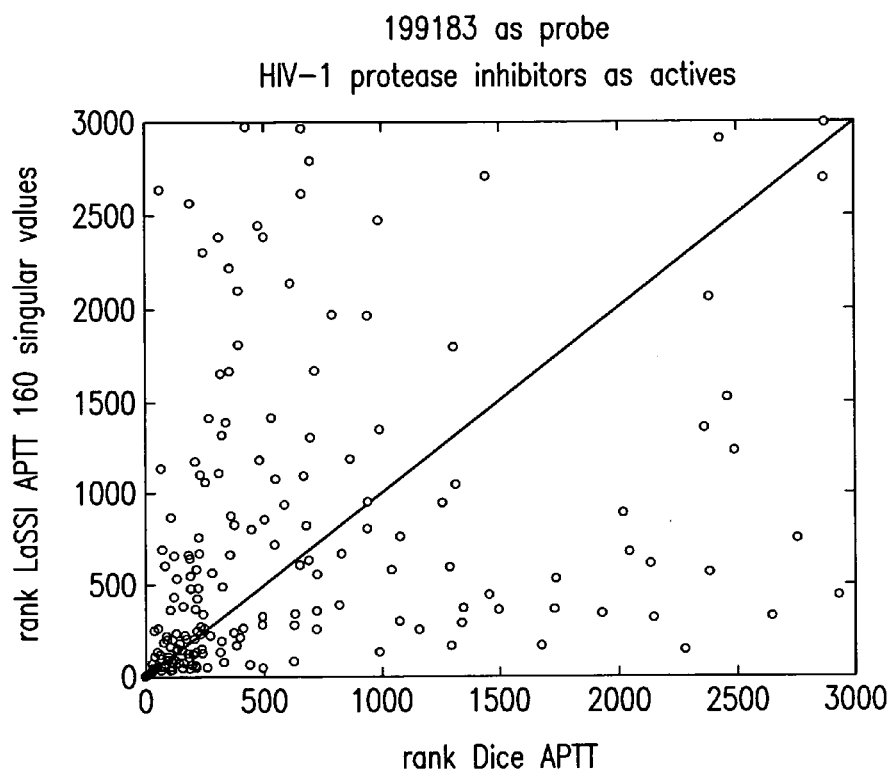
FIG. 9 is a graph showing a correlation of rank for the Dice and LaSSI methodologies.
Figure 10:
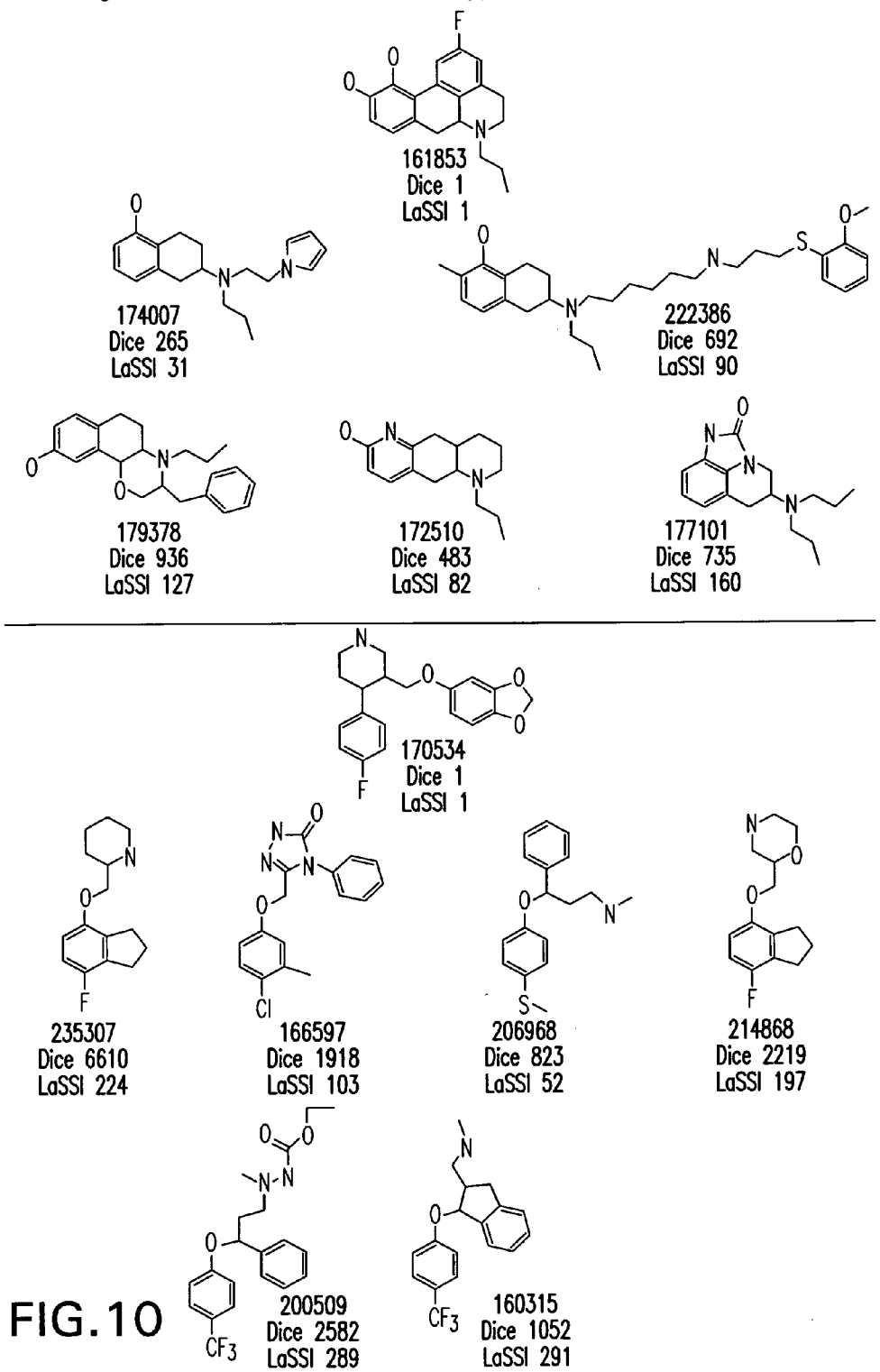
FIG. 10 shows selected compounds having different ranks according to the Dice and LaSSI methodologies.

When we compare the ranks of actives by LaSSI and Dice, we see that there is little to no correlation for any of the probes. An example is shown in FIG. 9. The actives are scattered and do not fall near the diagonal. LaSSI is clearly selecting very different actives than Dice. We can select molecules with strikingly different ranks by calculating disparity=log(rank Dice/rank LaSSI). FIG. 10 shows examples from three probes where abs(disparity) at least 0.5 (the ranks differ by a factor of more than −3) and one of the ranks at least 300 and the other less than or equal to 300.

Diversity of Actives

Figure 11:
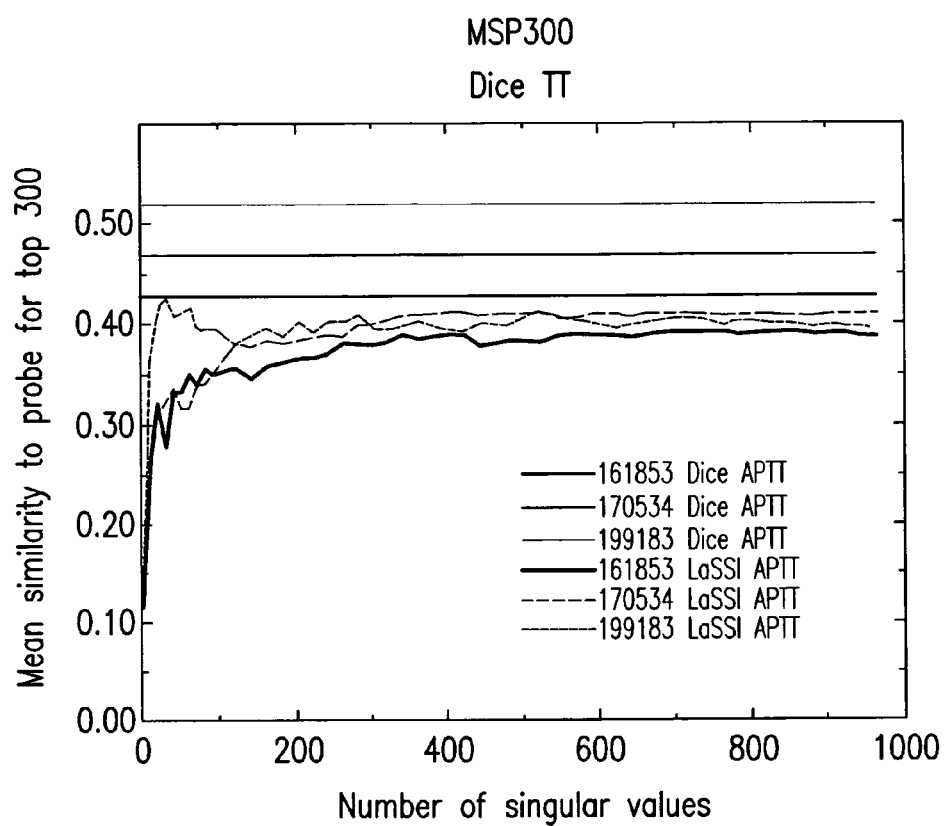
FIG. 11 is a graph of a mean similarity of a probe compound to each chemical molecule in the top scoring 300 compounds.

FIG. 11 shows the MSP300 as a function of number of singular values for three probes. For any given probe, the MSP300 for LaSSI is somewhat lower than MSP300 for the Dice, indicating an extra bit of "fuzziness" provided by LaSSI. For all probes, we have found the MSP300 for LaSSI is fairly constant until the number of singular values goes below about 20. In other words, for most singular values, LaSSI finds different actives than Dice in the top 300, but the diversity of the picks are not very much larger. For very low numbers of singular values, there is much more fuzziness in the results provided by the LaSSI methodology.

Selection of Non-Peptides Using a Peptide Probe

LaSSI has the potential of finding non-peptide actives given a peptide probe. Again we looked at initial enhancement as a function of number of singular values, this time taking into account only the non-peptide actives. Since the number of actives in the top 300 tends to be small, there tends to be more than one local maximum and other criteria need to be used. We chose as "best" the lowest number of singular values where the number of actives was a local maximum, and where the lowest ranking actives looked the least peptide-like. Generally the best number of singular values is very small (e.g., less than 20). This is consistent with the "fuzziness" of LaSSI increasing only at low numbers of singular values.

Figure 12:
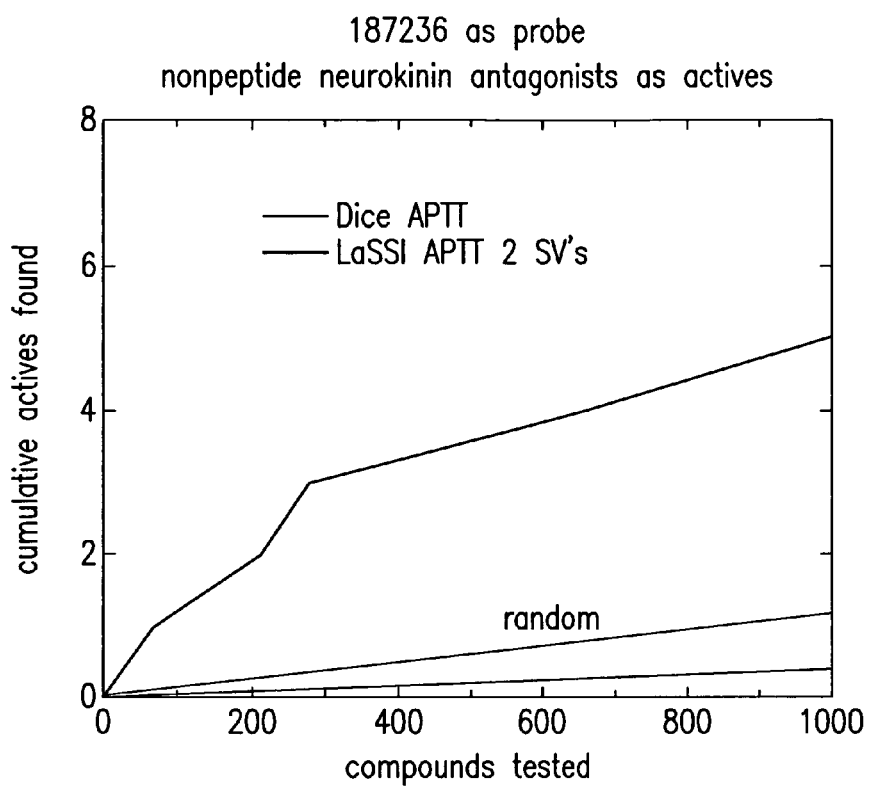
FIG. 12 is a graph of cumulative actives found versus compounds tested.

FIG. 12 shows the accumulation of non-peptide actives as a function of rank for the 187236 non-peptide example. Although overall the Dice curve is fairly hyperbolic at a large scale, i.e. the global enhancement is high, at ranks below a few thousand it falls below the diagonal. This is because the front of the list is highly enriched in peptides of any activity. In other words, to Dice nearly any peptide resembles a peptide oxytocin antagonist probe more than a non-peptide oxytocin antagonist does. The non-peptide actives are displaced to higher ranks, i.e., the initial enhancement is low. In contrast, on a large scale the LaSSI curve tends to drift toward the random line, i.e., the global enhancement is low. However, at low ranks the curve falls well above the random line, i.e., the initial enhancement is high. This is typical behavior for the peptide to non-peptide problem.

The figures of merit are shown in Table 7.

TABLE 7

Enhancements for peptide probes selecting non-peptide active

| Probe | Initial enhancement Dice APTT | Initial enhancement LaSSI APTT | Best no. SV's for LaSSI APTT | Probability due to chance |
| --- | --- | --- | --- | --- |
| 159880 | 0 | 1.9 | 2 | 0.054 |
| 170958 | 0 | 2.0 | 7 | 1.000 |
| 174556 | 0 | 2.7 | 9 | 0.003* |
| 187236 | 0 | 9.4 | 2 | 0.006* |

TABLE 7-continued

Enhancements for peptide probes selecting non-peptide active

| Probe | Initial enhancement Dice APTT | Initial enhancement LaSSI APTT | Best no. SV's for LaSSI APTT | Probability due to chance |
| --- | --- | --- | --- | --- |
| 188541 | 0 | 8.5 | 15 | <0.001* |
| cycAII | 0 | 2.1 | 2 | 0.005* |

*significant

Consistent with the behavior of the Dice curves, the initial enhancement for Dice is zero, i.e., much worse than random, for all peptide probes. The initial enhancements for LaSSI are modest, e.g., all less than 10, compared to those for the standard similarity probes with LaSSI or Dice, which averages 30–40, but given the difficulty that Dice has, this is encouraging. When the initial enhancements get below ~10, it becomes necessary to check whether the initial enhancement could have come about by chance. For each probe, we generated 1000 control sets wherein the ranks of the actives have been randomly assigned. We then see what fraction of the control sets have as many or more actives in the top 300 as the real search. Taking a probability of 0.05 as the cutoff above which the initial enhancement is not due to chance, we see that LaSSI does much better than chance for four out of six examples, with one near miss. Another type of control is to systematically assign the wrong activity to the ranked list. For example, we can calculate the initial enhancement for the ranked list for 187236 using the list of angiotensin II blockers instead of the correct list of neurokinin antagonists. With the exception of the 170958 example, which is clearly not significant, the right activity always gives a much higher initial enhancement than does any of the wrong activities.

FIG. 13 shows the molecules which have the most disparate ranks in the significant peptide to non-peptide examples. Clearly, the molecules in this figure resemble drug-like molecules more than they do oligopeptides. On the other hand, one can pick some salient features seen in the peptide probes, although the topological distance between the features is not the same in the peptide and non-peptide and the exact nature of the groups is different.

Discussion of the Comparison Study and the Results Thereof

Similarity searches are the most useful early in a drug-discovery project when few actives are known and little is known about what features of these molecules confer activity. It has been our experience that it is always useful to try different methods of calculating similarity, since each has a potentially "different" view of chemistry. In the realm of small molecule probes, LaSSI certainly selects different actives than does Dice, and is thus, a useful complement to TOPOSIM.

The fact that LaSSI, unlike Dice, has the number of singular values as an adjustable parameter adds flexibility but also introduces a complication. The goodness of the results can be sensitive to this parameter and the optimum number of singular values varies unpredictably from problem to problem. Fortunately, since LaSSI is so fast to run, it is a trivial matter to run several searches at different number of singular values.

LaSSI has the novel ability to help select non-peptide actives given a peptide probe when the number of singular values is low. We believe that the range of acceptable singular values for this application appears narrow. Most topological similarity methods based on atom-level descriptors have not been able to do this. This is basically because the backbone accounts for many of the descriptors and therefore dominates the similarity. Also, because the active conformation of peptides is often compact, e.g., beta-turns, the topological distances are often not correlated with the through-space distances. By adjusting the number of singular values downward, one can set LaSSI so that it captures the important features of a peptide and "blurs" out the atomic detail, including topological distance.

Having the ability to go from a peptide to non-peptides in a topological search is very desirable. Often in medicinal chemistry, an investigator has only peptide leads, but cannot develop a drug from it since peptides have poor transport properties. He or she needs to find non-peptide actives. The only way to find them by searching a database has been by 3-D similarity methods and/or 3-D substructure searching. However, for 3-D similarity it is necessary to construct a three-dimensional model of the peptide probe, and requires enough experimental information to specify its active conformation. Generating a pharmacophore for a 3-D substructure search query usually requires several semi-rigid analogs. This type of data is hard to get. Also, 3-D similarity methods are a few orders of magnitude slower than topological methods. Thus, although LaSSI's ability to find non-peptide actives might be modest compared to more expensive methods, there is an important application for LaSSI early in a project when structural and SAR data is lacking.

Figure 14:
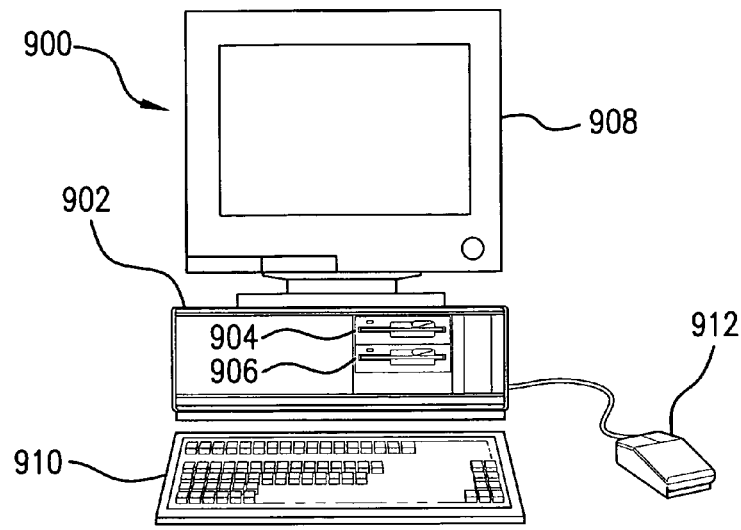
FIG. 14 is an illustrative embodiment of a computer and assorted peripherals.

FIG. 14 is an illustration of a main central processing unit for implementing the computer processing in accordance with a computer implemented embodiment of the present invention. The procedures described herein are presented in terms of program procedures executed on, for example, a computer or network of computers.

Viewed externally in FIG. 14, a computer system designated by reference numeral 900 has a computer 902 having disk drives 904 and 906. Disk drive indications 904 and 906 are merely symbolic of a number of disk drives which might be accommodated by the computer system. Typically, these would include a floppy disk drive 904, a hard disk drive (not shown externally) and a CD ROM indicated by slot 906. The number and type of drives varies, typically with different computer configurations. Disk drives 904 and 906 are in fact optional, and for space considerations, are easily omitted from the computer system used in conjunction with the production process/apparatus described herein.

The computer system also has an optional display 908 upon which information is displayed. In some situations, a keyboard 910 and a mouse 902 are provided as input devices to interface with the central processing unit 902. Then again, for enhanced portability, the keyboard 910 is either a limited function keyboard or omitted in its entirety. In addition, mouse 912 optionally is a touch pad control device, or a track ball device, or even omitted in its entirety as well. In addition, the computer system also optionally includes at least one infrared transmitter and/or infrared received for either transmitting and/or receiving infrared signals, as described below.

Figure 15:
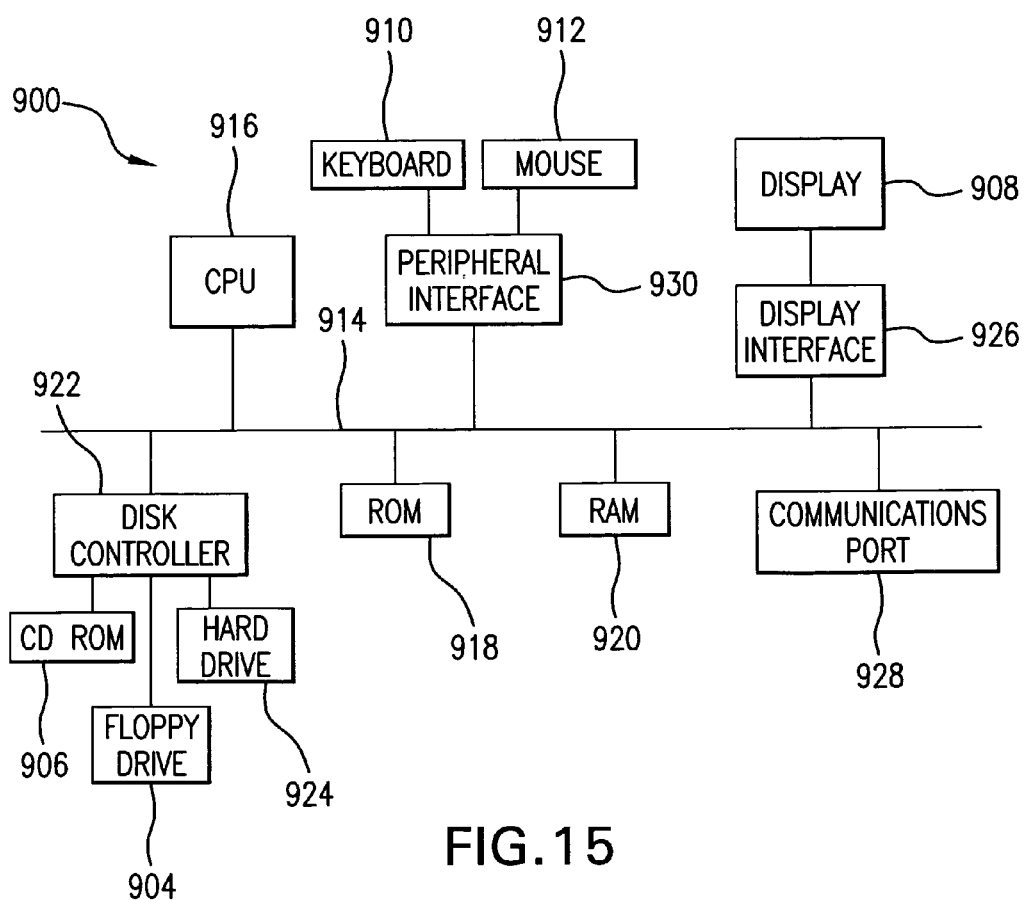
FIG. 15 is an illustrative embodiment of internal computer architecture consistent with the instant invention.

FIG. 15 illustrates a block diagram of the internal hardware of the computer system 900 of FIG. 14. A bus 914 serves as the main information highway interconnecting the other components of the computer system 900. CPU 916 is the central processing unit of the system, performing calculations and logic operations required to execute a program. Read only memory (ROM) 918 and random access memory (RAM) 920 constitute the main memory of the computer. Disk controller 922 interfaces one or more disk drives to the system bus 914. These disk drives are, for example, floppy disk drives such as 904, or CD ROM or DVD (digital video disks) drive such as 906, or internal or external hard drives 924. As indicated previously, these various disk drives and disk controllers are optional devices.

A display interface 926 interfaces display 908 and permits information from the bus 914 to be displayed on the display 908. Again as indicated, display 908 is also an optional accessory. For example, display 908 could be substituted or omitted. Communications with external devices, for example, the components of the apparatus described herein, occurs utilizing communication port 928. For example, optical fibers and/or electrical cables and/or conductors and/or optical communication (e.g., infrared, and the like) and/or wireless communication (e.g., radio frequency (RF), and the like) can be used as the transport medium between the external devices and communication port 928. Peripheral interface 930 interfaces the keyboard 910 and the mouse 912, permitting input data to be transmitted to the bus 914.

In addition to the standard components of the computer, the computer also optionally includes an infrared transmitter and/or infrared receiver. Infrared transmitters are optionally utilized when the computer system is used in conjunction with one or more of the processing components/stations that transmits/receives data via infrared signal transmission. Instead of utilizing an infrared transmitter or infrared receiver, the computer system optionally uses a low power radio transmitter and/or a low power radio receiver. The low power radio transmitter transmits the signal for reception by components of the production process, and receives signals from the components via the low power radio receiver. The low power radio transmitter and/or receiver are standard devices in industry.

Figure 16:
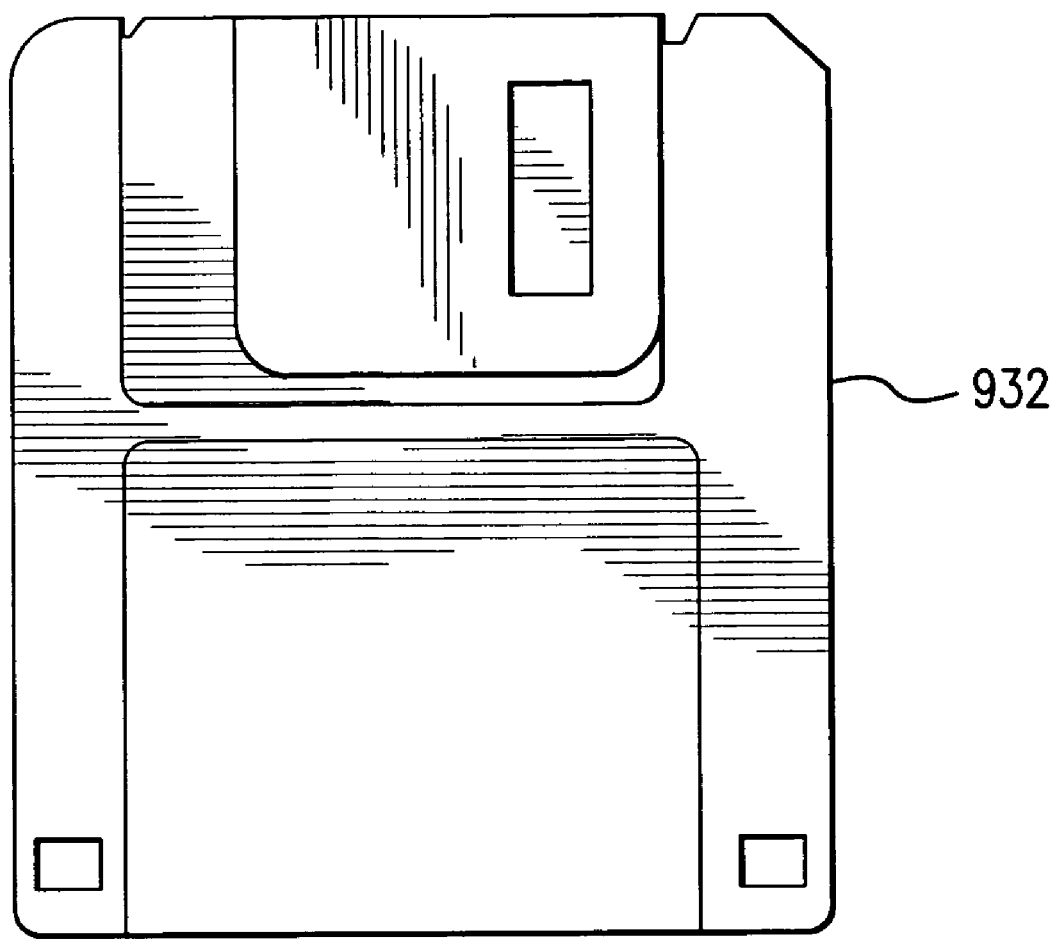
FIG. 16 is an illustrative embodiment of a memory medium.

FIG. 16 is an illustration of an exemplary memory medium 932 which can be used with disk drives illustrated in FIGS. 14 and 15. Typically, memory media such as floppy disks, or a CD ROM, or a digital video disk will contain, for example, a multi-byte locale for a single byte language and the program information for controlling the computer to enable the computer to perform the functions described herein. Alternatively, ROM 918 and/or RAM 920 illustrated in FIGS. 14 and 15 can also be used to store the program information that is used to instruct the central processing unit 916 to perform the operations associated with the production process.

Although computer system 900 is illustrated having a single processor, a single hard disk drive and a single local memory, the system 900 is optionally suitably equipped with any multitude or combination of processors or storage devices. Computer system 900 is, in point of fact, able to be replaced by, or combined with, any suitable processing system operative in accordance with the principles of the present invention, including sophisticated calculators, and hand-held, laptop/notebook, mini, mainframe and super computers, as well as processing system network combinations of the same.

Conventional processing system architecture is more fully discussed in *Computer Organization and Architecture*, by William Stallings, MacMillan Publishing Co. (3rd ed. 1993); conventional processing system network design is more fully discussed in *Data Network Design*, by Darren L. Spohn, McGraw-Hill, Inc. (1993), and conventional data communications is more fully discussed in *Data Communications Principles*, by R. D. Gitlin, J. F. Hayes and S. B.

Weinstain, Plenum Press (1992) and in *The Irwin Handbook of Telecommunications*, by James Harry Green, Irwin Professional Publishing (2nd ed. 1992). Each of the foregoing publications is incorporated herein by reference. Alternatively, the hardware configuration is, for example, arranged according to the multiple instruction multiple data (MIMD) multiprocessor format for additional computing efficiency. The details of this form of computer architecture are disclosed in greater detail in, for example, U.S. Pat. No. 5,163,131; Boxer, A., Where Buses Cannot Go, IEEE Spectrum, February 1995, pp. 41–45; and Barroso, L. A. et al., RPM: A Rapid Prototyping Engine for Multiprocessor Systems, IEEE Computer February 1995, pp. 26–34, all of which are incorporated herein by reference.

In alternate preferred embodiments, the above-identified processor, and, in particular, CPU 916, may be replaced by or combined with any other suitable processing circuits, including programmable logic devices, such as PALs (programmable array logic) and PLAs (programmable logic arrays). DSPs (digital signal processors), FPGAs (field programmable gate arrays), ASICs (application specific integrated circuits), VLSIs (very large scale integrated circuits) or the like.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

REFERENCES—INCORPORATED HEREIN BY REFERENCE

1. Carhart, R. E.; Smith, D. H.; Venkataraghavan, R. Atom pairs as molecular features in structure-activity studies: definition and applications. *J. Chem. Inf. Comp. Sci.* 1985, 25:64–73.
2. Nilakantan, R.; Bauman, N.; Dixon, J. S; Venkataraghavan, R. Topological torsions: a new molecular descriptor for SAR applications. Comparison with other descriptors. J. Chem. Inf. Comp. Sci 1987, 27:82–85.
3. Willet, P. Similarity and clustering in chemical information systems. Research Studies Press Ltd., John Wiley & Sons, New York, 1987, 254 pgs.
4. Deerwester, S.; Dumais, S. T.; Furnas, G. W.; Landuaer, T. K.; Harshman R. Indexing by Latent Semantic Analysis. *J. American Society for Information Science,* 1990, 41(6): 391–407.
5. Kearsley, S. K.; Sallamack, S.; Fluder, E. M.; Andose, J. D.; Mosley, R. T.; Sheridan, R. P. Chemical similarity using physiochemical property descriptors. *J. Chem. Inf. Comp. Sci.* 1996, 36:118–127.
6. MACCS Drug Data report licensed by Molecular Design Ltd., San Leandro, Calif.
7. Spear, K. L; Brown, M. S.; Reinhard, E. J.; McMahon, E. G.; Olins, G. M.; Palomo, M. A.; Patton, D. R. "Conformational restriction of angiotensin II: cyclic analogs having high potency." J. Med. Chem., 1990, 33, 1935–1940.

What is claimed is:

1. A method for calculating the similarity of at least one chemical compound to at least one chemical probe, comprising the steps of:
   (a) utilizing at least one chemical descriptor for each of a plurality of compounds, each descriptor comprising a row of a molecule-descriptor matrix X;
   (b) representing each compound as a column of the molecule-descriptor matrix, the entries of the molecule-descriptor matrix comprising a frequency of each descriptor for each compound;
   (c) performing a partial singular value decomposition (SVD) of the molecule-descriptor matrix to produce resultant matrices P, $\Sigma$, and $Q^T$, comprising:
   generating the resultant matrices P, $\Sigma$, and $Q^T$, such that molecule-descriptor matrix $X = P\Sigma Q^T$, wherein:
   P is a mxr matrix, called the left singular matrix, where r is the rank of X, and its columns are eigenvectors of $XX^T$ corresponding to nonzero eigenvalues:
   Q is a nxr matrix, called the right singular matrix, whose columns are eigenvectors of $X^TX$ corresponding to the nonzero eigenvalues; and
   $\Sigma$ is a rxr diagonal matrix whose nonzero elements, $\sigma_1, \sigma_2, \ldots, \sigma_r$, called singular values, are the square roots of the nonzero eigenvalues and have the property that $\sigma_1 \geq \sigma_2 \geq \ldots \geq \sigma_r$;
   (d) creating a chemical probe descriptor matrix for the at least one chemical probe, the entries of the chemical probe descriptor matrix comprising a frequency of each descriptor for each chemical probe;
   (e) calculating the similarity between the at least one chemical probe and at least one compound of the molecule descriptor matrix by:
   generating a reduced dimension approximation of X of rank k, defined as $X_k = P_k \Sigma_k Q^T_k$, wherein k<r and $\Sigma_k$ is an identity matrix;
   generating a pseudo-object, denoted as $O_F$, where $O_F = F^T P_k \Sigma^{-1}_k$, and where F is a molecule-descriptor vector for the at least one chemical probe; and
   taking a dot product of $O_F$ with one or more columns of $O^T_k$ respectively corresponding to the at least one compound; and
   (f) providing an output indicating the similarity between the at least one chemical probe and the at least one compound.

2. The method as recited in claim 1, wherein each of the at least one chemical descriptors comprise at least one of an atom pair descriptor and a topological torsion descriptor.

* * * * *